United States Patent
Gil et al.

(10) Patent No.: US 7,910,739 B2
(45) Date of Patent: Mar. 22, 2011

(54) ACETYLCHOLINESTERASE DUAL INHIBITORS

(75) Inventors: Ana Martinez Gil, Madrid (ES); Isabel Dorronsoro Diaz, Madrid (ES); Laura Rubio Arrieta, Madrid (ES); Diana Alonso Gordillo, Madrid (ES); Ana Fuertes Huerta, Madrid (ES); Susana Morales-Alcelay, Madrid (ES); Maria Del Monte Millan, Madrid (ES); Esther Garcia Palomero, Madrid (ES); Paola Usan Egea, Madrid (ES); Celia De Austria, Madrid (ES); Miguel Medina Padilla, Madrid (ES); Pilar Munoz Ruiz, Madrid (ES)

(73) Assignee: Noscira, S.A. (ES)

(*) Notice: Subject to any disclaimer, the term of this patent is extended or adjusted under 35 U.S.C. 154(b) by 71 days.

(21) Appl. No.: 10/887,974

(22) Filed: Jul. 9, 2004

(65) Prior Publication Data

US 2005/0148621 A1 Jul. 7, 2005

(30) Foreign Application Priority Data

Jul. 9, 2003 (GB) .................................. 0316094.2

(51) Int. Cl.
*C07D 219/12* (2006.01)
*A61K 31/435* (2006.01)

(52) U.S. Cl. .................. 546/106; 546/105; 514/290

(58) Field of Classification Search .................. 546/106, 546/105; 514/297, 290
See application file for complete search history.

(56) References Cited

U.S. PATENT DOCUMENTS

2006/0142323 A1 6/2006 Gil

FOREIGN PATENT DOCUMENTS

| EP | 0 397 040 | | 11/1990 |
|---|---|---|---|
| JP | 3-47179 | | 2/1991 |
| JP | 5-500055 | | 1/1993 |
| JP | 9-512784 | | 12/1997 |
| WO | WO 91/02725 | | 3/1991 |
| WO | WO 95/23137 | | 8/1995 |
| WO | WO 01/17529 | | 3/2001 |
| WO | WO 0117529 | * | 3/2001 |
| WO | WO 03/033489 | | 4/2003 |
| WO | WO 2004/032929 | | 4/2004 |

OTHER PUBLICATIONS

Ana Castro et al Peripheral and Dual Binding Site Acetylcholinesterase inhibitors. 2001.*
Dorwald F. A. Side Reactions in Organic Synthesis, 2005, Wiley: VCH, Weinheim p. IX of Preface.*
John Kelly, 1998, The Alzheimer's disease, Tacrine Legacy.*
Agarwal et al., Synthetic Communications, 1993, vol. 23, No. 8, pp. 1101-1110.
Alvarez et al., J. Neurosci, 1998, vol. 18, pp. 3213-3223.
Bogdal et al., "Remarkable Fast N-Alkylation of Azaheterocycles under Microwave Irradiation in Dry Media", Heterocycles, 1997, vol. 45, pp. 715-722.
Bruce et al., Tetrahedron Letters, 1996, vol. 7, pp. 937-940.
CAPLUS: SciFinder—Structures, Aug. 22, 2007, 5 pages.
Carlier et al., J. Med. Chem., 1999, vol. 42, pp. 4225-4231.
Castro et al., Mini Rev. Med. Chem., 2001, vol. 1, pp. 267-272.
Ellman et al., Biochem. Pharmacol., 1961, vol. 7, pp. 88-95.
Evans et al., "Enantioselective Indole Friedel—Crafts Alkylations Catalyzed by Bis(oxazolinyl)pyridine—Scandlum(III) Triflate Complexes", J. Am. Chem. Soc., 2003. vol. 125, pp. 10780-10781.
Inestrosa et al., J. Neuron, 1996, vo.. 16, pp. 881-891.
Klunk et al., J. Hystochem, 1989, vol. 8, pp. 1293-1297.
Muñoz et al., FEBS Lett., 1999, vol. 450, pp. 205-209.
Padwa et al., Synthesis, 1994, vol. 9, pp. 993-1004.
Piazza et al., J. Med. Chem., 2003, vol. 46, pp. 2279-2282.
Recanatini et al., "SAR of 9-Amino-1,2,3,4-tetrahydroacridine-Based Acetylcholinesterase Inhibitors: Synthesis, Enzyme Inhibitory Activity, QSAR, and Structure-Based CoMFA of Tacrine Analogues", J. Med. Chem., 2000, vol. 43, pp. 2007-2018. Savini et al., "Novel and Potent Tacrine-Related Hetero- and Homobivalent Ligands for Acetylcholinesterase andButyrycholinesterase", Bioorganic & Medicinal Chemistry Letters, 2001, vol. 11, pp. 1779-1782.
U.S. Appl. No. 10/530,667, filed Dec. 19, 2005, Ana Martinez Gil.

* cited by examiner

*Primary Examiner* — Rita J Desai
(74) *Attorney, Agent, or Firm* — Kenneth H. Sonnenfeld; King & Spalding LLP

(57) ABSTRACT

The invention provides compounds of formula:

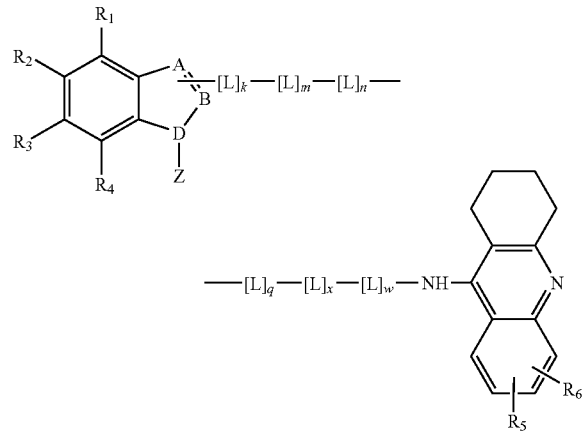

which have a tacrine moiety connected to an heterocyclic moiety through a linker. Through careful selection of the substituents and the linker, the activity and selectivity towards acetylcholinesterase can be modulated. The compounds show potent AChE inhibition activities together with modifications in the β-amyloid aggregation properties by binding simultaneously to the catalytic and peripheral AChE sites. They are useful in the treatment of AChE mediated diseases, such as the Alzheimer's disease.

21 Claims, No Drawings

ACETYLCHOLINESTERASE DUAL INHIBITORS

FIELD OF THE INVENTION

This invention relates to a series of tacrine derivatives, to processes for their preparation, to pharmaceutical compositions containing them, and to their medical use. In particular it relates to compounds and compositions which show dual site acetylcholinesterase inhibition, specially to be useful for the treatment of Alzheimer's disease.

CROSS REFERENCE TO RELATED APPLICATIONS

This application claims the benefit under 35 U.S.C. 119(a)-(d) of Great Britain Application No.: 0316094.2, filed on Jul. 9, 2003, the contents of which are incorporated herein by reference in its entirety.

BACKGROUND OF THE INVENTION

Alzheimer's disease (AD) is a progressive neurodegenerative disorder which is one of the most common causes of mental deterioration in elderly people, accounting for about 50-60% of the overall cases of dementia among persons over 65 years of age. Demographic data indicate that the percentage of elderly in the population is increasing.

Brain regions that are associated with higher mental functions, particularly the neocortex and hippocampus, are those most affected by the characteristic pathology of AD. This includes the extracellular deposits of β-amyloid (derived from amyloid precursor protein, APP) in senile plaques, intracellular formation of neurofibrillary tangles (containing an abnormally phosphorylated form of a microtubule associated protein, tau), and the loss of neuronal synapsis and pyramidal neurons.

Current treatment approaches in this disease continue being primarily symptomatic, with the major therapeutic strategy being based on the cholinergic hypothesis and specifically on acetylcholinesterase (AChE) inhibition. Over last decade, the cholinergic hypothesis of AD has launched on the market various cholinergic drugs primarily AChE inhibitors as tacrine, donepezil or rivastigmine, and more recently galanthamine, with modest improvement in the cognitive function of Alzheimer's patients. These compounds still present some undesired side effects such as nausea and vomiting.

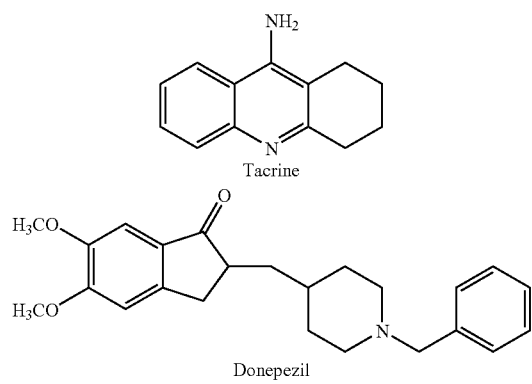

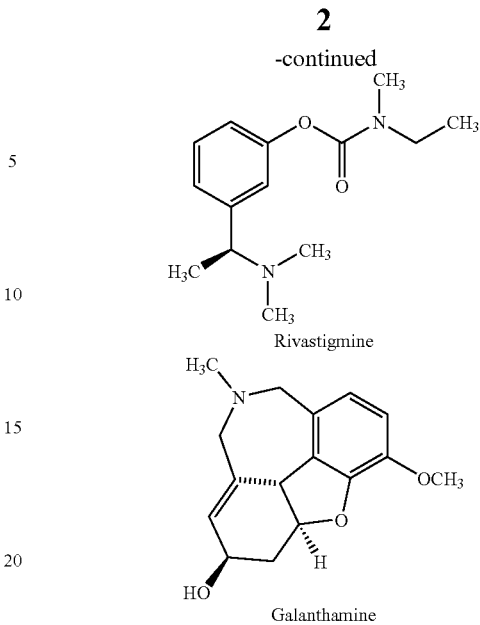

The three dimensional structure of AChE, as determined by X-ray crystallography, revealed that its active site can apparently be reached only through a deep and narrow catalytic gorge. Inhibitors of AChE act on two target sites on the enzyme, the active site and the peripheral site. Inhibitors directed to the active site prevent the binding of a substrate molecule, or its hydrolysis, either by occupying the site with a high affinity molecule (tacrine) or by reacting irreversibly with the catalytic serine (organophosphates and carbamates). The peripheral site consists of a less well-defined area, located at the entrance of the catalytic gorge. Inhibitors that bind to that site include small molecules, such as propidium and peptide toxins as fasciculins. Bis-quaternary inhibitors as decamethonium, simultaneously bind to the active and peripheral sites, thus occupying the entire catalytic gorge.

Parallel to the development of antidementia drugs, research efforts have been focused, among others, on the therapeutic potential of AChE inhibitors to slow the disorder progression. This fact was based on a range of evidence, which showed that AChE has secondary non-cholinergic functions.

New evidence shows that AChE may have a direct role in neuronal differentiation. Additionally, the role of AChE in cell adhesion have been studied. The results indicate that AChE promotes neurite outgrowth in neuroblastoma cell line through a cell adhesive role.

Moreover, recent studies have shown that the peripheral anionic site of the AChE is involved in the neurotrophic activity of the enzyme and conclude that the adhesion function of AChE is located at the peripheral anionic site. This finding has implications, not only for our understanding of neural development and its disorders, but also for the treatment of neuroblastoma, the leukemias, and especially for Alzheimer's disease.

As it has been previously mentioned, senile plaques are one of pathological hallmarks in AD in which their main component is βA peptide. This is found as an aggregated poorly soluble form. In contrast soluble βA is identified normally circulating in human body fluids. Structural studies of βA showed that synthetic peptides containing the sequences 1-40 and 1-42 of βA can adopt two major conformational states in solution: an amyloidogenic conformer (βA ac) with a high content of β-sheet and partly resistant to proteases and a non-amyloidogenic conformer βA nac) with a random coil conformation or β-helix and protease-sensitive. AChE colocalized with βA peptide deposits present in the brain of Alzheimer's patients. It is postulated that AChE binds to a βA nac form acting as a pathological chaperone and inducing a conformational transition from βA nac into βA ac in vitro and therefore to amyloid fibrils. AChE directly promotes the assembly of βA peptide into amyloid fibrils forming stable βA-AChE complexes.

Considering the non-cholinergic aspects of the cholinergic enzyme AChE, their relationship to Alzheimer's hallmarks and the role of the peripheral site of AChE in all these functions, an attractive target for the design of new antidementia drugs emerged. Peripheral or dual site inhibitors of AChE may simultaneously alleviate the cognitive deficit in Alzheimer's patients and what it is more important, avoid the assembly of beta-amyloid which represents a new way to delay the neurodegenerative process.

Thus, ligands able to interact simultaneously with active and peripheral sites could implicate several advantages over the known inhibitors. On one hand, they should improve greatly the inhibitory potency and on the other had they should be involved in neurotrophic activity.

Very recently some compounds have been reported with both activities, see Piazzi L. et al., *J. Med. Chem.*, 2003, 46, 2279-2282.

WO 03033489 describes piperidine derivatives having an effect of inhibiting acetylcholinesterase and aggregation of beta-amyloid.

WO 0117529 discloses halogen substituted tacrine or bistacrine derivatives for treating Alzheimer's disease. One of the subgroups presents an indole moiety connected to the tacrine through a short linker. For example, it describes the preparation of N-[2-(3-indolyl)ethyl]-6-chlorotacrine of formula:

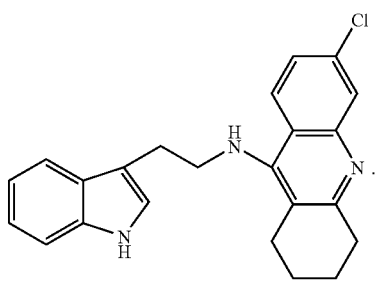

WO 0117529 does not suggest a site of inhibition and does not give any activity data.

Castro, A.; Martinez, A. *Mini Rev. Med. Chem.*, 2001, 1, 267-272 describe several families of peripheral and dual binding site AChE inhibitors, including some tacrine derivatives.

WO 04032929 discloses dual binding site AChE inhibitors containing a tacrine moiety connected through a linker to specified heterocycles such as a tacrine, an indanone or a thiadiazolidinone moiety.

SUMMARY OF THE INVENTION

After careful investigation we have designed a structurally distinct class of dual AChE inhibitors, i.e. compounds that, following the above ideas, show potent AChE inhibition activities together with modifications in the β-amyloid aggregation properties by binding simultaneously to the catalytic and peripheral AChE sites. In addition, their selectivity can be modulated and they present low toxicity which makes them candidates for drug development.

The compounds of the invention are characterised by the presence of two main heterocyclic units: a tacrine moiety and a [6+5] heteroaromatic moiety, connected through an appropriate linker. We have found that selectivity and activity can be modulated with the nature and length of the linker, and the nature and substituents of the above mentioned moieties. As the examples show, such compounds present high AChE inhibition, low toxicity, high binding to the peripheral site and inhibition of β-amyloid aggregation and β-amyloid-AChE aggregation complex and, if desired, high selectivity.

In one aspect the invention is directed to a compound of formula (I):

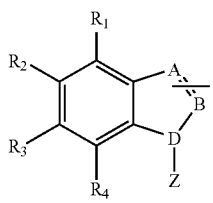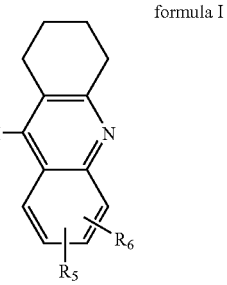

formula I wherein
A, B are independently selected from CH or N;
D is elected from CH, O, S, N;
provided that at least one of A, B or D is an heteroatom;
when D is CH or N, then Z is selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy,
when D is O or S, then Z is absent;
each L is independently selected from —$CR_aR_b$—, —$CR_a$=, —CO—, —O—, —S— or —$NR_a$—;
k, m, n, q, x and w are each an integer independently selected from 0, 1, 2, 3, 4, 5, 6, 7, 8, 9 or 10, with the proviso that k+m+n+q+x+w is at least 4;
$R_1$ to $R_6$ are independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, —$COR_a$, —$C(O)OR_a$, —$C(O)NR_aR_b$, —C=NR$_a$, —CN, —OR$_a$, —OC(O)R$_a$, —S(O)$_t$—R$_a$, —NR$_a$R$_b$, —NR$_a$C(O)R$_b$, —NO$_2$, —N=CR$_a$R$_b$ or halogen;

R$_a$ and R$_b$ are each independently selected from hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy or halogen; with the proviso that they are not halogen when linked to a N;

t is 0, 1 or 2;

or a tautomer, a pharmaceutically acceptable salt, a prodrug or a solvate thereof.

The side chain of formula:

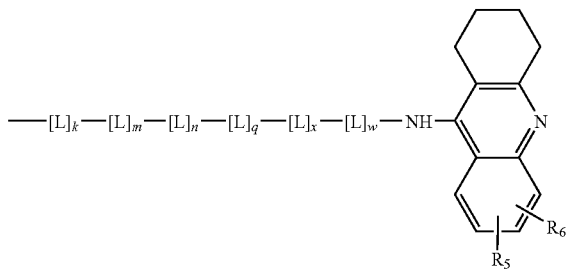

is suitably a substituent on A or B when A or B is carbon, which then becomes C in place of CH.

In another aspect the invention is directed to pharmaceutical compositions which comprise a compound according to formula (I) or a pharmaceutically acceptable salt, prodrug or solvate thereof, and a pharmaceutically acceptable carrier, adjuvant or vehicle. In a preferred embodiment the formulation is oral.

The present invention is also directed to the use of the above defined compounds in the manufacture of a medicament, preferably for the treatment of cognitive disorders such as senile dementia, cerebrovascular dementia, mild recognition impairment, attention deficit disorder, and/or neurodegenerative dementing disease with aberrant protein aggregations such as especially Alzheimers's disease or condition, or prion disease as Creutzfeld-Jacob disease or Gerstmann-Straussler-Scheinher disease, or Parkinson's disease or condition, or Polyglutamine disease, or tauopathies such as Pick's disease, frontotemporal dementia, supranuclear progressive palsy, or familial amyotrophic lateral sclerosis or systemic amyloidosis or condition.

In another embodiment the invention is directed to the use of the above defined compound in a method of treatment of these diseases or conditions.

In another aspect, the invention is directed to the use of the above defined compounds as reactives for biological assays.

In another aspect the invention is directed to a process for preparing a compound of formula I above by coupling the two heterocyclic moieties through the linker.

DETAILED DESCRIPTION OF THE INVENTION

In the above definition of compounds of formula (I) the following terms have the preferred meaning indicated:

"Alkyl" refers to a straight or branched hydrocarbon chain radical consisting of carbon and hydrogen atoms, containing no saturation, having one to eight carbon atoms, and which is attached to the rest of the molecule by a single bond, e.g., methyl, ethyl, n-propyl, i-propyl, n-butyl, t-butyl, n-pentyl, etc. Alkyl radicals may be optionally substituted by one or more substituents such as a halo, hydroxy, alkoxy, carboxy, cyano, carbonyl, acyl, alkoxycarbonyl, amino, nitro, mercapto and alkylthio.

"Amino" refers to a radical of the formula-NH$_2$, —NHR$_a$ or —NR$_a$R$_b$, wherein R$_a$ and R$_b$ are as defined above.

"Aryl" refers to a phenyl, naphthyl, indenyl, phenanthryl or anthracyl radical, preferably phenyl or naphthyl radical. The aryl radical may be optionally substituted by one or more substituents such as hydroxy, mercapto, halo, alkyl, phenyl, alkoxy, halo alkyl, nitro, cyano, dialkylamino, aminoalkyl, acyl and alkoxycarbonyl.

"Aralkyl" refers to an aryl group linked to an alkyl group. Preferred examples include benzyl and phenethyl.

"Acyl" refers to a radical of the formula-C(O)—R$_c$ or —C(O)—R$_d$ where R$_c$ is an alkyl radical and R$_d$ is an aryl radical, e.g., acetyl, propionyl, benzoyl, and the like. Other acyl groups are possible.

"Cycloalkyl" refers to a 3- to 10-membered monocyclic or bicyclic radical which is saturated or partially saturated, and which consist of carbon and hydrogen atoms. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy and alkoxycarbonyl.

"Fused aryl" refers to an aryl group, especially a phenyl or heteroaryl group, fused to another ring.

"Alkoxy" refers to a radical of the formula-OR$_a$ where R$_a$ is an alkyl radical as defined above, e.g., methoxy, ethoxy, propoxy, etc.

"Hal-" or "Halo" refers to bromo, chloro, iodo or fluoro.

"Heterocyclyl" refers to a 3- to 15 membered ring radical which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran.

References herein to substituted groups in the compounds of the present invention refer to the specified moiety that may be substituted at one or more available positions by one or more suitable groups, e.g., halogen such as fluoro, chloro, bromo and iodo; cyano; hydroxyl; nitro; azido; alkanoyl such as a C$_{1-6}$ alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atom; alkoxy groups having one or more oxygen linkages and from 1 to about 12 carbon atoms or 1 to about 6 carbon atoms; aryloxy such as phenoxy, alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocyclic aryl having 6 or more carbons, particularly phenyl or naphthyl and aralkyl such as benzyl. Unless otherwise indicated, an optionally substituted group may have a substituent at each substitutable position of the group, and each substitution is independent of the other.

In the compounds of the invention the [6+5] heteroaromatic moiety can be selected among others from indole, isoindole, benzimidazole, indazole, benzothiophene, benzotriazole, benzoisoxazole, benzofurane, isobenzofurane.

A preferred class of compounds of formula (I) is that in which A and preferably also B are CH. D is preferably N.

In a preferred embodiment the [6+5] heteroaromatic moiety is an indole or indazole unit, preferably a substituted or unsubstituted indole. In this case good results are obtained when the linker is connected to the position 2 or 3 of the indole unit, more preferably to the position 3. More generally, in one variation of the present invention, the linker is on a carbon of the hetero ring at a position adjacent to the benzene ring, being for example the 3 position of the indole. Such compounds are of the formula:

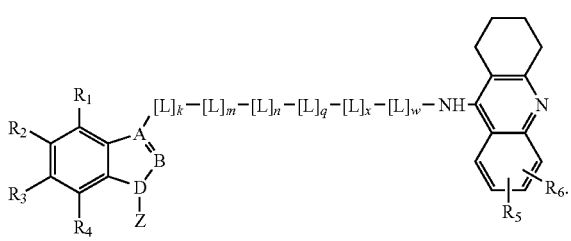

Another preferred class of compounds of formula (I) is that in which the tacrine moiety is substituted. More preferably it has a halogen substituent. In a preferred embodiment the tacrine moiety has a chloro substituent at position 6. This gives improved activity and selectivity towards AChE.

We have found that the linker between the two units plays an important role in the activity and selectivity. Indeed, a linker containing a number of L units in the range between 4 and 18, more preferably between 7 and 13 gives good results. Most preferred are values between 8 and 12, and specially of about 10 or 11.

In a preferred embodiment the linker -(L)$_k$-(L)$_m$-(L)$_n$-(L)$_q$-(L)$_x$-(L)$_w$- is selected from the formulae —(CH$_2$)$_k$—CO—NR$_a$—(CH$_2$)$_w$—, —(CH$_2$)$_k$—NR$_a$—CO—(CH$_2$)$_w$—, —(CH$_2$)$_k$—CO—NR$_a$—(CH$_2$)$_q$—NR$_a$—(CH$_2$)$_w$—, —(CH$_2$)$_k$—NR$_a$—CO—(CH$_2$)$_q$—NR$_a$—(CH2)$_w$—, —(CH$_2$)$_k$—O—CO—NR$_a$—(CH$_2$)$_w$— wherein k, q, w and R$_a$ are as defined above. More preferably, the linker -(L)$_k$-(L)$_m$-(L)$_n$-(L)$_q$-(L)$_x$-(L)$_w$- has the formulae —(CH$_2$)$_k$—CO—NR$_a$—(CH$_2$)$_w$— or —(CH$_2$)$_k$—O—CO—NR$_a$—(CH$_2$)$_w$—. R$_a$ is Usually H. The integer k is preferably 1 or 2, especially 2. The integer w is suitably from 6 to 9, especially 6 or 7.

It is preferred that the linker contains one or more amide units, they can be at any position in the linker.

It is to be understood that the present invention includes all combinations of the mentioned particular and preferred groups.

In one aspect, preferred compounds of this invention are of the formula (II):

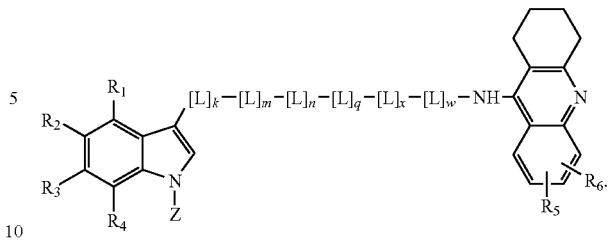

In a related aspect, more preferred compounds are of the formula (III):

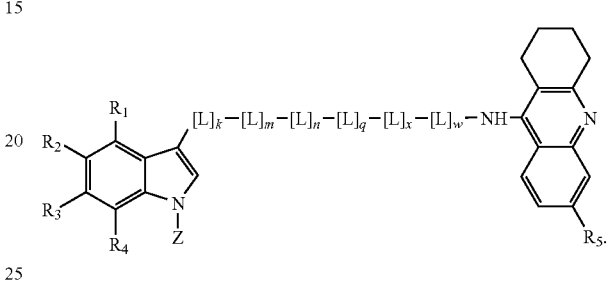

In the compounds of the various formulae of this invention, Z is preferably selected from H and CH$_3$, especially H. R$_1$, R$_3$ and R$_4$ are preferably H. R$_2$ is preferably selected from H, -Hal, and —CN, especially H. Preferably R$_5$ is halogen and R$_6$ is hydrogen.

In particular, we prefer that R$_1$, R$_2$, R$_3$, R$_4$, Z are hydrogen; R$_5$ is halogen especially chloro; and the linker includes an amido function, preferably an amido function flanked by oligomethylene groups. Thus, the linker is preferably of formula —(CH$_2$)$_k$—CONH—(CH$_2$)$_w$—, where the sum of k and w is preferably in the range 6 to 10, especially 7 to 9. Suitably k is less than w, with k being 1, 2 or 3.

As variants, R$_1$ to R$_5$ are independently selected from the group consisting of hydrogen, —CN, and halogen; and/or each L is independently selected from the group consisting of —CR$_a$R$_b$—, —CO— and —NR$_a$.

As a further aspects the present invention extends to compounds of the formula (A):

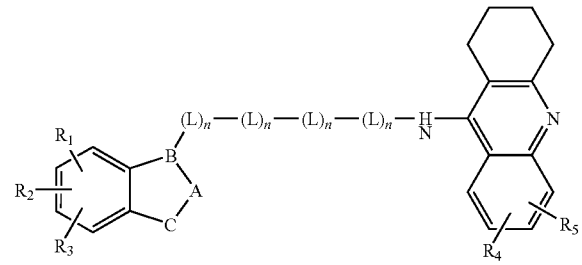

Where:
L is independently selected from —C(R')(R")—, —CO—, —O— or —NR'—
n is zero, one, two, three, four, five, six, seven, eight, nine or ten
R' and R" are independently selected from hydrogen, alkyl, aryl, heteroaryl, halo, haloalkyl, alkoxy, alkylthio
A is independently selected from —CO—, —C(R')(R")—, =C(R')—, —N(R')—, =N—, —O—, —S(O)t-

B is independently selected from —C(R')—, =C—, —N—,

C is independently selected from —C(R')(R")—, =C(R')—, —N(R')—, =N—, $R_1, R_2, R_3, R_4$ and $R_5$ are independently selected from hydrogen, alkyl, alkoxy, alkylthio; cycloaklyl, haloalkyl, halo, aryl, $-(Z)_n$-aryl, heteroaryl, —$OR_3$, —$C(O)R_3$, —$C(O)OR_3$, —$S(O)_t$, cyano, nitro, mercapto t is zero, one or two Z is independently selected from $C(R_3)(R_4)$—, —C(O)—, —O—, —$C(=NR_3)$—, —$S(O)_t$—, $N(R_3)$—.

In a related aspect, the compounds of this invention are in agreement with both the formula (I) and the formula (A). Such compounds are of the formula (B):

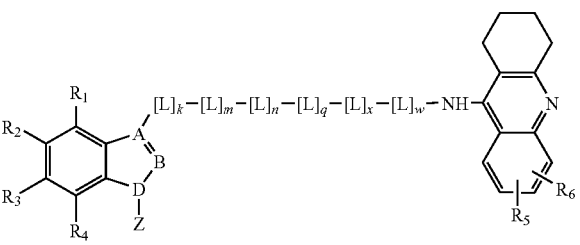

where the respective definitions are selected to overlap with those of both formula (I) and formula (A).

Preferably for the formula (B), the following definitions will apply:

A is CH or N;
B is CH or N;
D is CH, O, S or N;
at least one of A, B and D is a heteroatom;
Z is hydrogen alkyl, alkoxy, cycloalkyl, haloalkyl, aryl, aralkyl, heteroaryl;
$R_1, R_2, R_3, R_4, R_5, R_6$ are hydrogen, alkyl, alkoxy, alkylthio, cycloalkyl, haloalkyl, halo, aralkyl, heteraryl, $OR_3$, $COR_3$, $COOR_3$, $SO_tR_3$ where t is 0, 1 or 2;
at least one of $R_1, R_2, R_3, R_4$ is hydrogen;
L is $CR_aR_r$; CO, O, $NR_a$ where $R_a$ and $R_r$ are hydrogen, alkyl, aryl, heteroaryl, halo, haloalkyl, alkoxy,
k, m, n, q, x and w are 0 to 10, provided that the total is not more than 40 and preferably x and w are 0.

Unless otherwise stated, the compounds of the invention are also meant to include compounds which differ only in the presence of one or more isotopically enriched atoms. For example, compounds having the present structures except for the replacement of a hydrogen by a deuterium or tritium, or the replacement of a carbon by a $^{13}$C— or $^{14}$C-enriched carbon or $^{15}$N-enriched nitrogen are within the scope of this invention.

The term "pharmaceutically acceptable salts, derivatives, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminum and lithium salts, and organic alkali salts such as, for example, ethylenediamine, ethanolamine, N,N-dialkylenethanolamine, triethanolamine, glucamine and basic aminoacids salts.

Particularly favoured derivatives or prodrugs are those that increase the bioavailability of the compounds of this invention when such compounds are administered to a parent (e.g., by allowing an orally administered compound to be more readily absorbed into the blood) or which enhance delivery of the parent compound to a biological compartment (e.g., the brain or lymphatic system) relative to the parent species.

Any compound that is a prodrug of a compound of formula (I) is within the scope of the invention. The term "prodrug" is used in its broadest sense and encompasses those derivatives that are converted in vivo to the compounds of the invention. Such derivatives would readily occur to those skilled in the art, and include, depending on the functional groups present in the molecule and without limitation, the following derivatives of the present compounds: esters, amino acid esters, phosphate esters, metal salts sulfonate esters, carbamates, and amides.

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

The compounds of formula (I) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), or of its salts, solvates or prodrugs.

The compounds of the present invention represented by the above described formula (I) may include enantiomers depending on the presence of chiral centres or isomers depending on the presence of multiple bonds (e.g. Z, E). The single isomers, enantiomers or diastereoisomers and mixtures thereof fall within the scope of the present invention.

The compounds of formula (I) defined above can be obtained by a convergent pathway strategy by coupling the two heterocyclic moieties which contain part of the linker. Synthetic procedures to obtain the intermediates containing the tacrine moiety or the benzofused 5 ring heterocyclic system are available in the literature and involve standard organic synthesis procedures. The person skilled in the art of organic synthesis will readily design the process for each compound depending on the desired functionality of the heterocycles and the nature of the linker to be obtained. See for example WO 0117529 and WO04032929. Other intermediates are reported in the literature.

9-alkylaminotetrahydroacridines can be synthesized following the previously reported procedures [Carlier, P. R.; Chow. E. S.-H; Han, Y.; Liu, J.; El Yazal, J.; Pang Y.-P. *J. Med. Chem.*, 1999, 42, 4225-4231]. The general method for the synthesis of indole derivatives was previously described in Padwa A. et al, *Synthesis*, 1994, 9, 993-1004. 5-Cyanoindole-3-propionic acid can be synthesized according to the method reported in the literature [Agarwal, A.; Jalluri, R. K.; Dewitt Blanton, C.; and Will Taylor, B., *Synthetic communications*, 1993, 23, 8, 1101-1110]. Alternative heterocycles can be prepared and used. General methods of organic synthesis are available for example in "March's Advanced Organic Chemistry: Reactions, Mechanisms, and Structure" 5th Edition Wiley; Wiley series "The Chemistry of Heterocyclic Compounds"; Wiley Series "Compendium of Organic Synthetic methods", etc.

Schemes 1 and 2 exemplify processes for the preparation of compounds of the invention when the linker contains an amide or a carbamate bond:

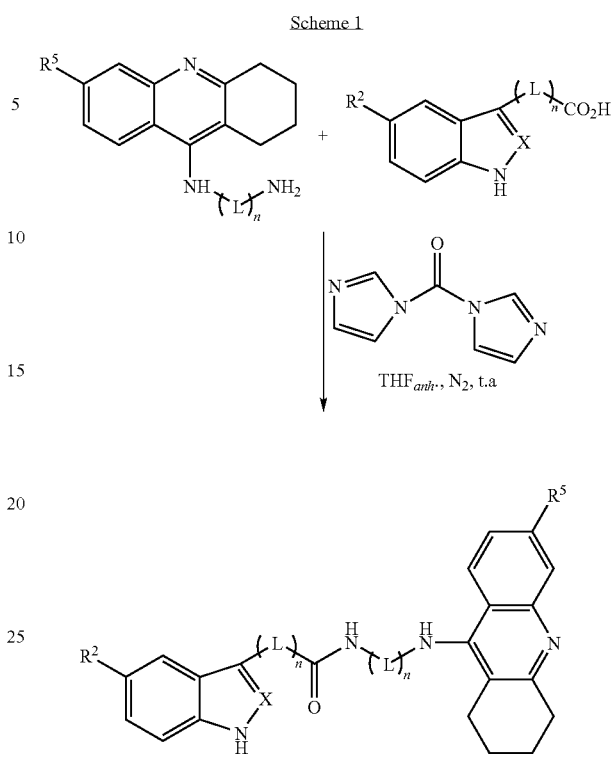

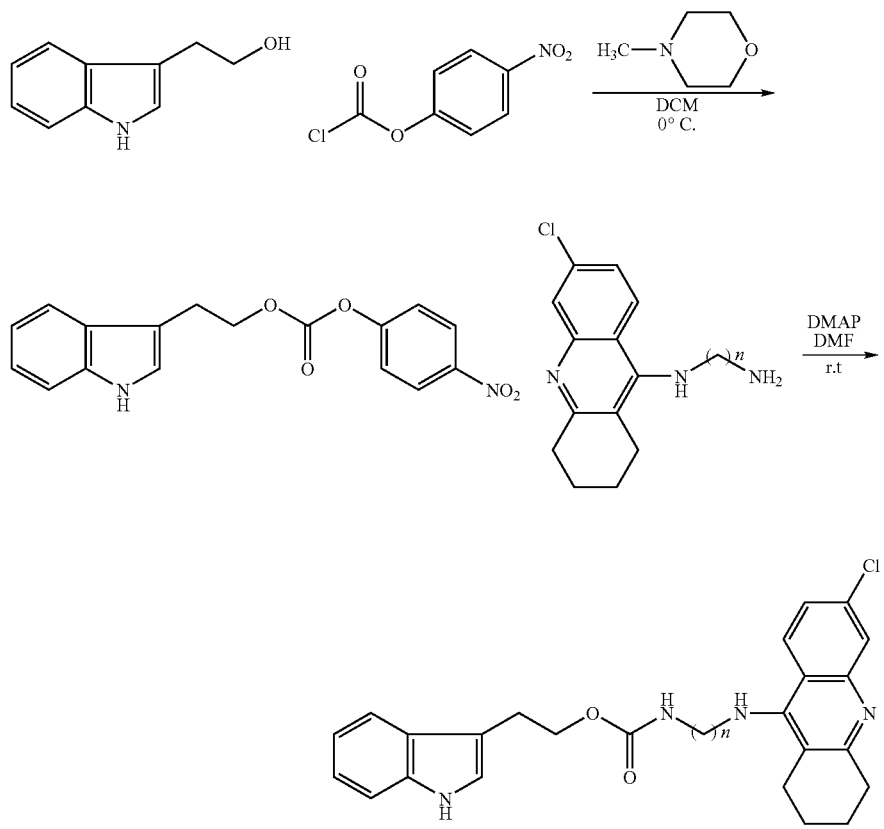

Alternative processes for compounds with amine, ether, ester or other units in the linker will be readily apparent to the skilled person.

For example to a solution of the corresponding indole derivative in anhydrous THF was added 1,1'-carbonyldiimidazole under $N_2$, and the resulting mixture was stirred for 4 hours at room temperature. A solution of the corresponding 9-alkylaminotetrahydroacridine in THF was added and the stirring was continued for further 20 hour. After evaporation of the solvent under reduced pressure, water was added and the resulting mixture was extracted with dichloromethane. The combined organic extracts were washed with saturated NaCl solution and dried with $Na_2SO_4$. Evaporation of the solvent under reduced pressure gave a residue which was purified by silica gel flash-column chromatography as indicated bellow for each case.

The reaction products may, if desired, be purified by conventional methods, such as crystallization or chromatography. Where the above described processes for the preparation of compounds of the invention give rise to mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in a pharmaceutical composition. In the case of salts and solvates the additional ionic and solvent moieties must also be non-toxic. The compounds of the invention may present different polymorphic forms, it is intended that the invention encompasses all such forms.

The typical compounds represented by the abovementioned formula (I) of the present invention, a salt thereof, a solvate or a prodrug of them exhibit a superior acetylcholinesterase inhibitory action. Therefore, another aspect of this invention relates to a method of treating, improving or preventing an AChE related disease or condition which method comprises administering to a patient in need of such a treatment a therapeutically effective amount of a compound of formula (I) or a pharmaceutical composition thereof. Among the diseases that can be treated are cognitive disorders as senile dementia, cerebrovascular dementia, mild recognition impairment, attention deficit disorder, and/or neurodegenerative dementing disease with aberrant protein aggregations as specially Alzheimers's disease or condition, or prion disease as Creutzfeld-Jacob disease or Gerstmann-Straussler-Scheinher disease, or Parkinson's disease or condition, or Polyglutamine disease, or tauopathies as Pick's disease, frontotemporal dementia, supranuclear progressive palsy, or familial amyotrophic lateral sclerosis or systemic amyloidosis or condition.

The present invention further provides pharmaceutical compositions comprising a compound of this invention, or a pharmaceutically acceptable salt, derivative, prodrug or stereoisomers thereof together with a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the apropriate unit dosage form. Adequate excipients can be used, such as bulking agents, buffering agents or surfactants.

The mentioned formulations will be prepared using standard methods such as those described or referred to in the Spanish and US Pharmacopoeias and similar reference texts.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

Generally an effective administered amount of a compound of the invention will depend on the relative efficacy of the compound chosen, the severity of the disorder being treated the weight of the sufferer. However, active compounds wills typically be administered once or more times a day for example 1, 2, 3 or 4 times daily, with typical total daily doses in the range of from 0.1 to 1000 mg/kg/day. It will be appreciated that it may be necessary to make routine variations to the dosage, depending on the age and condition of the patient, and the route of administration.

The compounds and compositions of this invention may be used with other drugs to provide a combination therapy. The other drugs may form part of the same composition, or be provided as a separate composition for administration at the same time or at different time.

The following examples are given as further illustration of the invention, they should not be taken as a definition of the limits of the invention.

EXAMPLES

The general procedures for the preparation of compounds of the invention have been described above.

Example 1

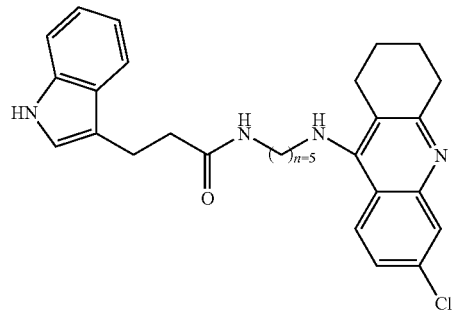

N-[5(6-Chloro-1,2,3,4-tetrahydro-acridin-9-ylamino) pentyl]-3-(1H-indol-3-yl) propionamide Reagents: Indole-3-propionic acid (57 mg, 0.3 mmol), THF anhydrous (3 ml), 1,1'-carbonyldiimidazol (51 mg, 0.32 mmol), and 6-chloro-9-(5-aminopentylamino)-1,2,3,4-tetrahydroacridine (100 mg, 0.32 mmol).

Purification: silica gel column chromatography using DCM/MeOH (7:1). Yellow solid, yield: 121 mg (83%).

$^1$H-NMR (CDCl$_3$, 400 MHz, δ ppm): 8.53 (brs, 1H), 7.87 (d, 1H, J=8.8 Hz), 7.88 (d, 1H, J=2.4 Hz), 7.55 (dd, 1H, J=8.0 Hz, J=1.2 Hz), 7.30 (dd, 1H, J=8.0 Hz, J=0.8 Hz), 7.21 (dd, 1H, J=8.8 Hz, J=2.4 Hz), 7.13 (td, 1H, J=8 Hz, J=1.2 Hz), 7.06 (td, 1H, J=8.0 Hz, J=0.8 Hz), 6.90 (m, 1H), 5.61 (m, 1H), 4.24 (brs, 1H), 3.43 (t, J=6.4 Hz), 3.16 (c, 2H, J=66.4 Hz), 3.10 (t, 2H, J=7.2 Hz), 3.01 (m, 2H), 2.52 (m, 2H), 2.56 (t, 2H, J=7.2 Hz), 1.84 (m, 4H), 1.60 (2H, m), 1.38 (m, 2H), 1.25 (m, 2H).

$^{13}$C-NMR (CDCl$_3$, 100 MHz, δ.ppm): 172.9, 159.0, 151.4, 147.9, 136.5, 134.6, 127.2, 126.6, 124.9, 124.5, 122.0, 121.9, 119.4, 118.7, 118.2, 115.4, 114.8, 111.4, 49.5, 39.4, 37.7, 33.6, 31.5, 29.6, 24.9, 24.3, 23.1, 22.7, 21.8. ESI-MS[M+H$^+$]$^+$ 489.

Example 2

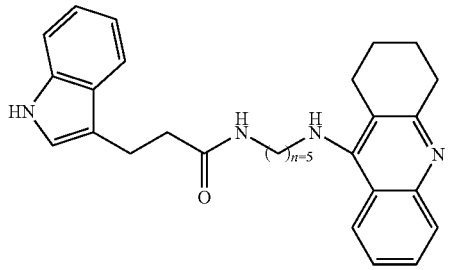

3-(1H-Indol-3-yl)-N-[5-(1,2,3,4-tetrahydro-acridin-9-ylamino)-pentyl]-propionamide Reagents: Indole-3-propionic acid (63 mg, 0.33 mmol), THF anhydrous (3 ml), 1,1'-carbonyldiimidazol (57 mg, 0.35 mmol), and 9-(5-aminopentylamino)-1,2,3,4-tetrahydroacridine (100 mg, 0.35 mmol).

Purification: silica gel column chromatography using DCM/MeOH (3:1). Yellow solid. Yield: 147 mg (97%).

$^1$H-NMR (CDCl$_3$, 400 MHz, δ ppm): 8.53 (brs, 1H), 7.90 (t, 2H, J=8.4 Hz), 7.55 (t, 1H, J=8.4 Hz), 7.52 (dd, 1H, J=8.0 Hz, J=0.8 Hz), 7.35 (t, 1H, J=8.4 Hz), 7.30 (dd, 1H, J=8.0 Hz, J=0.8 Hz), 7.13 (td, 1H, J=8 Hz, J=1.2 Hz), 7.05 (td, 1H, J=8.0 Hz, J=0.8 Hz), 6.90 (m, 1H), 5.61 (m, 1H), 3.90 (brs, 1H), 3.40 (m, 2H), 3.19 (c, 2H, J=6.4 Hz), 3.10 (t, 2H, J=7.2 Hz), 3.01 (m, 2H), 2.62 (m, 2H), 2.56 (t, 2H, J=7.2 Hz), 1.80-2.00 (m,4H), 1.60 (m, 2H), 1.38 (m, 2H), 1.25 (m, 2H.

$^{13}$C-NMR (CDCl$_3$, 100 MHz, δ ppm): 172.9, 158.6, 150.8, 147.0, 136.5, 128.9, 128.8, 127.0, 123.8, 123.0, 122.1, 122.0, 120.1, 119.4, 118.8, 116.2, 114.8, 111.4, 49.6, 39.5, 37.8, 34.4, 31.7, 29.7, 25.2, 24.5, 23.5, 23.2, 21.8. ESI-MS[M+H$^+$]$^+$ 455.

Example 3

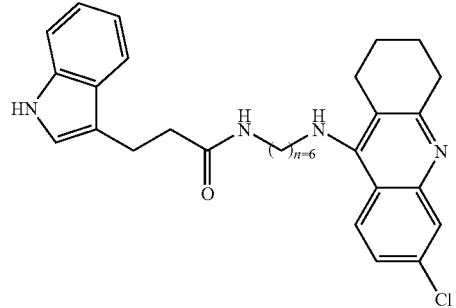

N[5-(6-Chloro-1,2,3,4-tetrahydro-acridin-9-ylamino) hexyl]-3-(1H-indol-3-yl)-propionamide Reagents: Indole-3-propionic acid (70 mg, 0.37 mmol), THF anhydrous (3 ml), 1,1'carbonyldiimidazol (63 mg, 0.39 mmol), and 6-chloro-9-(6-aminohexylamino)-1,2,3,4-tetrahydroacridine (131 mg, 0.39 mmol).

Purification: silica gel column chromatography using DCM/MeOH (50:1, 25:1, 20:1). Yellow solid. Yield: 143 mg (77%).

$^1$H-NMR (CDCl$_3$, 400 M δ ppm): 8.40 (brs, 1H), 7.85 (d, 1H, J=2.4 Hz), 7.84 (d, 1H, J=8.8 Hz), 7.55 (dd, 1H, J=8.0 Hz, J=1.2 Hz), 7.29 (dd, 1H, J=8.0 Hz, J=0.8 Hz), 7.23 (dd, 1H, J=8.8 Hz, J=2.4 Hz), 7.15 (td, 1H, J=8.0 Hz, J=1.2 Hz), 7.07 (td, 1H, J=8.0 Hz, J=0.8 Hz), 6.97 (m, 1H), 5.41 (m, 1H), 4.42 (brs, 1H), 3.41 (t, 2H, J=6.4 Hz), 3.13 (c, 2H, J=6.4 Hz), 3.09 (t, 2H, J=7.2 Hz), 3.01 (m, 2H), 2.64 (m, 2H), 2.54 (t, 2H, J=7.2 Hz), 1.91-1.88 (m, 4H), 1.59-1.53 (2H, m), 1.36-1.27 (m, 4H), 1.22-1.16 (m, 2H).

$^{13}$C-NMR (CDCl$_3$, 100 MHz, δ. ppm): 172.7, 159.4, 150.7, 148.0, 136.4, 134.0, 127.3, 127.1, 124.6, 124.2, 121.8, 119.1, 118.6, 118.4, 115.7, 114.7, 111.3, 49.5, 39.4, 37.6, 34.1, 31.8, 29.6, 26.6, 26.6, 24.8, 23.1, 22.8, 21.7. ESI-MS: m/z [M+H$^+$]$^+$ 503.

Example 4

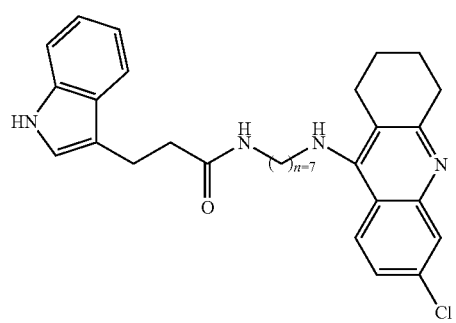

N-[7-(6-Chloro-1,2,3,4-tetrahydro-acridin-9-ylamino)-heptyl]-3-(1H-indol-3-yl)-propionamide Reagents: Indole-3-propionic acid (70 mg, 0.37 mmol), THF anhydrous (3 ml), 1,1'-carbonyldiimidazol (63 mg, 0.39 mmol), and 6-chloro-9-(7-aminoheptylamino) 1,2,3,4-tetrahydroacridine (135 mg, 0.39 mmol).

Purification: silica gel column chromatography using AcOEt/MeOH (50:1). Yellow solid. Yield: 151 mg (79%).

$^1$H-NMR (CDCl$_3$, 400 MHz, δ ppm): 8.10 (brs, 1H), 7.87 (d, 1H, J=8.8 Hz), 7.85 (d, 1H, J=2.4 Hz), 7.57 (dd, 1H, J=8.0 Hz, J=1.2 Hz), 7.32 (dd, 1H, J=8.0 Hz, J=0.8 Hz), 7.24 (dd, 1H, J=8.8 Hz, J=2.4 Hz), 7.16 (td, 1H, J=8 Hz, J=1.2 Hz), 7.09 (td, 1H, J=8.0 Hz, J=0.8 Hz), 6.99 (m, 1H), 5.32 (m, 1H), 3.91 (brs, 1H), 3.45 (t, 2H, J=6.4 Hz), 3.13 (c, 2H, J=6.4 Hz), 3.11 (t, 2H, J=7.2 Hz), 3.02 (m, 2H), 2.65 (m, 2H, 2.55 (t, 2H, J=7.2 Hz), 1.92-1.88 (m, 4H), 1.64-1.57 (m, 2H), 1.36-1.14 (m, 8H).

$^{13}$C-NMR (CDCl$_3$, 100 MHz δ ppm): 172.4, 159.3, 150.6, 147.9, 136.1, 133.8, 127.3, 126.9, 14.4, 124.0, 121.8, 121.6, 119.0, 118.5, 118.2, 115.6, 114.7, 111.0, 49.5, 39.3, 37.5, 34.0, 31.7, 29.4, 28.9, 26.7, 26.6, 24.6, 22.9, 22.7, 21.5. ESI-MS: m/z [M+H$^+$]$^+$ 517.

Example 5

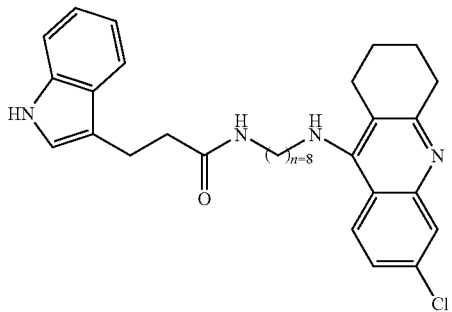

N-[8-(6-Chloro-1,2,3,4-tetrahydro-acridin-9-ylamino)-octyl]-3-(1H-indol-3-yl)propionamide Reagents: Indole-3-propionic acid (70 mg, 0.37 mmol), THF anhydrous (3 ml), 1,1'-carbonyldiimidazol (63 mg, 0.39 mmol), and 6-chloro-9-(8-aminooctylamino)-1,2,3,4-tetrahydroacridine (140 mg, 0.39 mmol).

Purification: silica gel column chromatography using. AcOEt/MeOH (50:1). Yellow solid. Yield: 104 mg (53%).

$^1$H-NMR (CDCl$_3$, 400 MHz δ ppm): 8.21 (brs, 1H, 7.86 (d, 1H, J=8.8 Hz), 7.85 (d, 1H, J=2.4 Hz), 7.57 (dd, 1H, J=8.0 Hz, J=1.2 Hz), 7.24 (dd, 1H, J=8.0 Hz, J=0.8 Hz), 7.24 (dd, 1H, J=8.8 Hz, J=2.4 Hz), 7.16 (td, 1H, J=8.0 Hz, J=1.2 Hz), 7.09 (td, 1H, J=8.0 Hz, J=0.8 Hz), 6.99 (m, 1H), 5.35 (m, 1H), 3.91 (brs, 1H), 3.46 (t, 2H, J=6.4 Hz), 3.14 (c, 2H, J=6.4 Hz), 3.10 (t, 2H, J=7.2 Hz), 3.01 (m, 2H), 2.65 (m, 2H), 2.55 (t, 2H, J=7.2 Hz), 1.92-1.89 (m, 4H), 1.64-1.58 (m, 2H), 1.36-1.31 (m, 4H), 1.28-1.14 (m, 6H).

$^{13}$C-NMR (CDCl$_3$, 100 MHz, δ. ppm): 172.6, 159.4, 150.8, 148.1, 136.4, 133.9, 127.4, 127.1, 124.6, 124.1, 121.9, 121.8, 119.1, 118.6, 118.4, 115.7, 114.8, 111.3, 49.7, 39.6, 37.7, 34.2, 31.9, 29.7, 29.3, 27.0, 26.8, 24.8, 23.1, 22.9, 21. ESI-MS: m/z [M+H$^+$]$^+$ 531.

Example 6

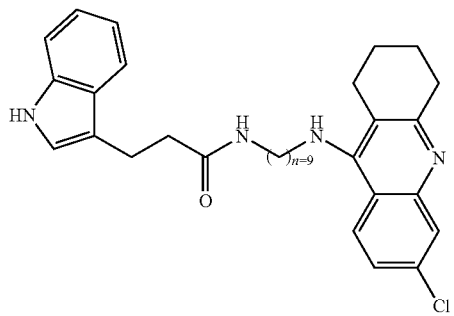

N-[9-(6-Chloro-1,2,3,4-tetrahydro-acridin-9-ylamino)-nonyl]-3-(1H-indol-3-yl)-propionamide Reagents: indole-3-propionic acid (28 mg, 0.15 mmol), THF anhydrous (3 ml), 1,1'-carbonyldiimidazol (25 mg, 0.15 mmol), and 6-chloro-9-(9-aminononylamino)-1,2,3,4-tetrahydroacridine (57 mg, 0.15 mmol).

Purification: silica gel column chromatography using. DCM/MeOH (7:1). Yellow solid. Yield: 10 mg (14%).

$^1$H-NMR (CDCl$_3$, 400 MHz, δ. ppm): 8.53 (brs, 1H), 7.87 (d, 1H, J=8.8 Hz), 7.88 (d, 1H, J=2.4 Hz), 7.57 (dd, 1H, J=8.0 Hz, J=1.2 Hz), 7.30 (dd, 1H, J=8.0 Hz, J=0.8 Hz), 7.21 (dd, 1H, J=8.8 Hz, J=2.4 Hz), 7.13 (td, 1H, J=8 Hz, J=1.2 Hz), 7.06 (td, 1H, J=8.0 Hz, J=0.8 Hz), 6.90 (m, 1H), 5.61 (m, 1H), 4.24 (brs, 1H), 3.50 (m, 2H), 3.19 (c, 2H, J=6.4 Hz), 3.10 (t, 2H, J=7.2 Hz), 3.01 (m, 2H), 2.62 (m, 2H), 2.56 (t, 2H, J=7.2 Hz), 1.81 (m,4H), 1.52 (m, 2H), 1.01-1.40 (m, 13H).

$^{13}$C-NMR (CDCl$_3$, 100 MHz, δ ppm): 172.7, 159.0, 151.2, 147.8, 136.5, 134.3, 127.3, 127.2, 125.0, 124.4, 122.1, 122.0, 119.3, 118.8, 118.2, 115.3, 115.0, 111.4, 49.8, 39.8, 37.8, 34.0, 32.0, 29.8, 29.7, 29.5, 29.5, 27.2, 27.1, 25.0, 23.4, 23.0, 22.0. ESI-MS[M+H$^+$]$^+$ 545.

Example 7

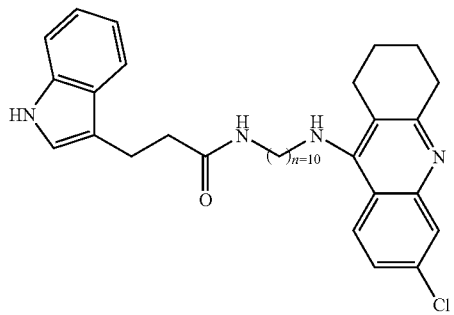

N-[10-(6-Chloro-1,2,3,4-tetrahydro-acridin-9-ylamino)-decyl]-3-(1H-indol-3-yl)-propionamide Reagents: indole-3-propionic acid (47 mg, 0.25 mmol), THF anhydrous (4 ml), 1,1'-carbonyldiimidazol (44 mg, 0.27 mmol), and 6-chloro-9-(10-aminodecylamino)-1,2,3,4-tetrahydroacridine (105 mg, 0.27 mmol).

Purification: silica gel column chromatography using DCM/MeOH (10:1). Yellow solid. Yield: 21 mg (19%).

¹H-NMR (CDCl₃, 400 Mz, δ. ppm): 8.63 (brs, H), 7.89 (d, 1H, J=8.8 Hz), 7.87 (d, 1H, J=2.4 Hz), 7.56 (dd, 1H, J=8.0 Hz, J=1.2 Hz), 7.32 (dd, 1H, J=8.0 Hz, J=0.8 Hz), 7.21 (dd, 1H, J=8.8 Hz, J=2.4 Hz), 7.14 (td, 1H, J=8 Hz, J=1.2 Hz), 7.08 (td, 1H, J=8.0 Hz, J=0.8 Hz), 6.97 (m, 1H), 5.61 (m, 1H), 4.24 (brs, 1H), 3.50 (m, 2H), 3.19 (c, 2H, J=6.4 Hz), 3.10 (t, 21, J=7.2 Hz), 3.01 (m, 2H), 2.63 (m, 2H), 2.56 (t, 2H, J=7.2 Hz), 1.80-2.00 (m,4H), 1.51 (m, 2H), 1.01-1.40 (m, 14H).

¹³C-NMR (CDCl₃, 100 MHz, δ. ppm): 172.7, 159.0, 151.2, 147.8, 136.5, 134.3, 127.3, 127.2, 125.0, 124.4, 122.1, 122.0, 119.3, 118.8, 118.2, 115.3, 115.0, 111.4, 49.8, 39.8, 37.8, 34.0, 32.0, 29.8, 29.7, 29.6, 29.5, 29.5, 27.2, 27.1, 25.0, 23.4, 23.0, 22.0. ESI-MS[M+H⁺]⁺ 559.

Example 8

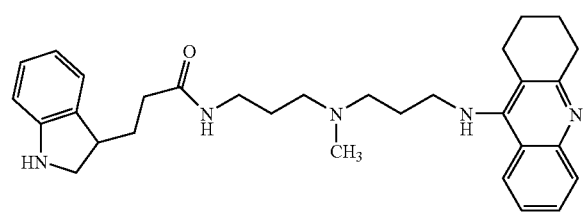

N-(3-{[3-(1,2,3,4-tetrahydro-acridin-9-ylamino)-propyl]-methyl-amino}-propyl)-3-(1H-indol-3-yl) propionamide Reagents: Indole-3-propionic acid (56 mg, 0.29 mmol), THF anhydrous (4 ml), 1,1'carbonyldiimidazol (50 mg, 0.31 mmol), and N¹-[3-(1,2,3,4-tetrahydro-acridin-9-ylamino)-propyl]-N¹-methyl-propane-1,3-diamine (100 mg, 0.31 mmol).

Purification: silica gel column chromatography using DCM/MeOH (20:1+0.1% NH₃, 10:1+0.2% NH₃, 10:1+0.4% NH₃. Yellow solid. Yield: 70 mg (46%).

¹H-NMR (CDCl₃, 400 MHz, δ. ppm): 8.80 (brs, 1H), 7.86 (t, 2H, J=8.4 Hz), 7.51 (t, 1H, J=8.4 Hz), 7.46 (d, 1H, J=8.4 Hz), 7.27 (td, 1H, J=7.0 Hz, J=2.0 Hz), 7.25 (d, 1H, 7.0 Hz), 7.10 (td, 1H, J=8.0 Hz, J=1.2 Hz), 7.03 (td, 1H, J=8.0 Hz, J=1.2 Hz), 6.85 (d, 1H, J=2.4 Hz), 6.37 (t, 1H, J=4.5 Hz), 5.00 (brs, 1H), 3.46 (m, 2H), 3.19 (c, 2H, J=6.3 Hz), 3.07-3.01 (m, 4H), 2.63 (m, 2H), 2.47 (t, 2H, J=7.0), 2.36 (t, 2H, J=6.4 Hz), 2.24 (t, 2H, J=6.8 Hz), 1.91 (s, 3H), 1.86-1.84 (m, 4H), 1.70-1.67 (m, 2H), 1.54-1.50 (m, 2H).

¹³C-NMR (CDCl₃, 100 MHz, δ. ppm): 172.0, 158.3, 150.8, 147.2, 136.3, 128.4, 128.3, 127.1, 123.6, 122.8, 121.8, 121.8, 120.2, 119.0, 118.5, 115.9, 114.7, 111.3, 56.6, 56.1, 48.7, 42.2, 38.5, 37.7, 34.0, 28.5, 26.6, 25.3, 23.2, 22.9, 21.7. ESI-MS: m/z [M+H⁺]⁺ 498.

Example 9

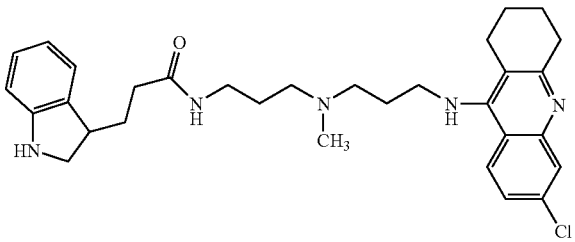

N-(3-{[3-(6-chloro-1,2,3,4-tetrahydro-acridin-9-ylamino)-propyl]-methyl-amino}-propyl)-3-(1H-indol-3-yl)-propionamide Reagents: indole-3-propionic acid (56 mg, 0.29 mmol), THF anhydrous (4 ml), 1,1'-carbonyldiimidazol (50 mg, 0.31 mmol), and N¹-[3-(6-Chloro-1,2,3,4-tetrahydro-acridin-9-ylamino)-propyl]-N¹-methyl-propane-1,3-diamine (100 mg, 0.31 mmol).

Purification: silica gel column chromatography using DCM/MeOH (20:1+0.1% NH₃, 10:1+0.2% NH₃, 10:1+0.4% NH₃). Yellow solid. Yield: 70 mg (46%).

¹H-NMR (CDCl₃, 400 MHz, δ ppm): 8.79 (br, 1H), 7.83 (d, 1H, J=8.8 Hz), 7.79 (d, 1H, J=2.4 Hz), 7.30 (dd, 1H, J=8.0 Hz, 1.2 Hz), 7.24 (dd, 1H, J=8.0 Hz, 0.8 Hz), 7.14 (dd, 1H, J=8.8 Hz, 2.4 Hz), 7.08 (td, 1H, 0.8 Hz, J=1.2 Hz), 7.01 (td 1H, J=8.0 Hz, J=0.8 Hz), 6.86 (m, 1H), 6.30 (m, 1H), 3.91 (brs, 1H), 3.45 (m, 2H), 3.17 (c, 2H, J=7.2 Hz), 3.03 (t, 2H, J=6.4 Hz), 2.94 (m, 2H), 2.50 (m, 2H), 2.46 (t, 2H, J=7.2 Hz), 2.41-2.23 (m, 2H), 2.22-2.18 (m, 2H), 2.10 (s, 3H), 1.18 (m, 4H), 1.73-1.60 (m, 2H), 1.59-1.49 (m, 2H).

¹³C-NMR (CDCl₃, 100 MHz, δ. ppm): 172.7, 159.5, 151.0, 148.0, 136.4, 134.0, 127.3, 127.2, 124.7, 124.1, 121.9, 122.0, 119.2, 118.6, 118.4, 115.7, 114.8, 111.4, 56.7, 56.21, 49.0, 42.3, 38.6, 37.8, 34.2, 28.5, 26.8, 25.2, 23.2, 23.0, 21.8. ESI-MS: m/z [M+H⁺]⁺ 531.

Example 10

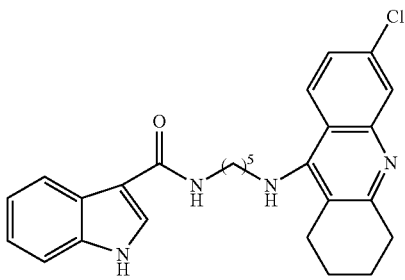

1H-Indole-3-carboxylic acid [5-(6-chloro-1,2,3,4-tetrahydro-acridin-9-ylamino)-pentyl]-amide Reagents: Indole-3-carboxylic acid (151 mg, 0.94 mmol), THF anhydrous (4 ml), 1,1'-carbonyldiimidazol (153 mg, 0.94 mmol), and 6-chloro-9-(8-aminopentylamino)-1,2,3,4-tetrahydroacridine (276 mg, 0.90 mmol).

Purification: silica gel column chromatography (eluent: EtOAc/MeOH 50:1). Yellow solid. Yield: 198 mg (52%).

$^1$H-NMR (CD$_3$OD, 400 MHz, δ. ppm): 8.07 (d, 1H, J=9.0 Hz), 8.06 (d t, 1H, J=8.0 Hz and J=0.8 Hz), 7.80 (s, 1H), 7.69 (d, 1H, J=2.0 Hz), 7.41 (d, 1H, J=8.0 Hz), 7.22 (dd, 1H, J=9.0 Hz and J=2.0 Hz), 7.17 (td, 1H, J=8.0 Hz and J=1.2 Hz), 7.12 (td, 1H, J=8.0 Hz and J=1.2H 3.58 (t, 2H, J=7.0 Hz), 3.37 (t, 2H, J=7.0 Hz), 2.88 (t, 2H, J=6.2 Hz), 2.65 (t, 2H, J=6.2 Hz), 1.79 (m, 4H), 1.71 (m, 2H), 1.63 (m, 2H), 1.45 (m, 2H).

$^{13}$C-NMR (CD$_3$OD, 100 MHz, δ ppm): 168.6, 160.3, 153.4, 148.6, 138.2, 135.6, 128.9, 127.2, 126.7, 126.6, 125.1, 123.5, 122.0, 121.8, 119.5, 116.7, 112.9, 112.0, 40.1, 34.3, 32.0, 30.7, 26.1, 25.4, 24.0, 23.6. ESI-MS[M]$^+$ 461.07.

Example 11

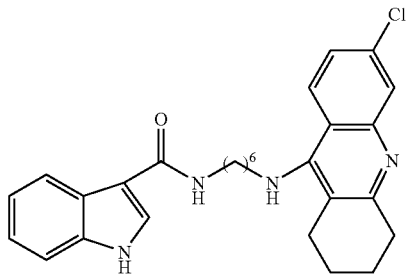

1H-Indole-3-carboxylic acid [6-(6-chloro-1,2,3,4-tetrahydro-acridin-9-ylamino)-hexyl]-amide Reagents: Indole-3-carboxylic acid (153 mg, 0.95 mmol), THF anhydrous (10 ml), 1,1'-carbonyldiimidazol (154 mg, 0.95 mmol), and 6-chloro-9-(8-aminohexylamino)-1,2,3,4-tetrahydroacridine (300 mg, 0.90 mmol).

Purification: silica gel column chromatography (eluent: EtOAc/MeOH 50:1). Yellow solid. Yield: 120 mg (28%).

$^1$H-NMR (CDCl$_3$, 400 MHz, δ ppm): 10.24 (brs, 1H), 7.89 (m, 1H), 7.85 (d, 1H, J=9.4 Hz), 7.83 (d, 1H, J=2.0 Hz), 7.71 (d, 1H, J=2.8 Hz), 7.39 (m, 1H), 7.18-7.22 (m, 3H), 6.13 (t, 1H, J=5.8 Hz), 4.0 (brs, 1H), 3.46 (m, 4H), 2.97 (m, 2H), 2.60 (m, 2H), 1.84 (m, 4H), 1.60 (m, 4H), 1.39 (m, 4H).

$^{13}$C-NMR (CD$_3$Cl, 100 MHz, δ ppm): 166.0, 159.6, 151.0, 148.1, 136.7, 134.2, 128.4, 127.2, 124.8, 114.7, 124.3, 122.8, 121.5, 119.7, 118.3, 115.7, 112.4, 112.1, 49.5, 39.4, 33.9, 31.7, 30.0, 26.7, 26.6, 24.6, 22.9, 22.6. ESI-MS[M+H]$^+$ 476.

Example 12

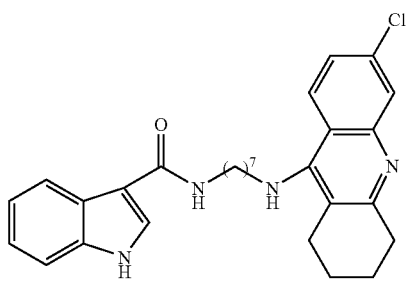

1H-Indole-3-carboxylic acid [7-(6-chloro-1,2,3,4-tetrahydro-acridin-9-ylamino)-heptyl]-amide Reagents: Indole-3-carboxylic acid (147 mg, 0.91 mmol), THF anhydrous (10 ml), 1,1'-carbonyldiimidazole (147 mg, 0.91 mmol), and 6-chloro-9-(8-aminoheptylamino)-1,2,3,4-tetrahydroacridine (300 mg, 0.87 mmol).

Purification: silica gel column chromatography (eluent: EtOAc/MeOH 50:1). Yellow solid. Yield: 226 mg (51%).

$^1$H-NMR (CDCl$_3$, 400 MHz, δ ppm): 9.88 (brs, 1H), 7.90 (dd, 1H, J=6.3 Hz, 3.0 Hz), 7.87 (d, 1H, J=9 Hz), 7.84 (d, 1H, J=2.0 Hz), 7.73 (d, 1H, J=2.7 Hz), 7.41 (dd, 1H, J=0.3 Hz, J=3.0 Hz), 7.23 (d, 1H, J=9 Hz), 7.23-7.19 (m, 2H), 6.06 (t, 1H, J=5.5 Hz), 4.0 (brs, 1 Hz), 3.46; (m, 4H), 2.98 (m, 2H), 2.61 (m, 2H), 1.85 (m, 4H), 1.59 (m, 4H), 1.34 (m, 6H).

$^{13}$C-NMR (CD$_3$Cl, 100 MHz, δ ppm): 165.7, 159.6, 151.1, 148.2, 136.6, 134.2, 128.3, 127.4, 124.8, 124.7, 124.3, 122.8, 121.6, 119.8, 118.4, 115.8, 112.4, 112.3, 49.6, 39.5, 34.0, 31.8, 29.9, 29.1, 27.0, 26.9, 24.7, 22.9, 22.7. ESI-MS[M]$^+$ 489.

Example 13

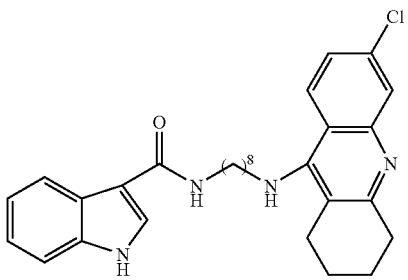

1H-Indole-3-carboxylic acid [8-(6-chloro-1,2,3,4-tetrahydro-acridin-9-ylamino) octyl]-amide.

Reagents: Indole-3 carboxylic acid (92 mg, 0.57 mmol), THF anhydrous (3 ml), 1,1'-carbonyldiimidazole (92 mg, 0.57 mmol), and 6-chloro-9-(8-aminooctylamino)-1,2,3,4-tetrahydroacridine (196 mg, 0.54 mmol).

Purification: silica gel column chromatography (eluent: Hexane/EtOAc 1:2+0.1% NH$_3$, 1:3+0.2% NH$_3$). Yellow solid. Yield: 110 mg (40%).

$^1$H-NMR (CDCl$_3$, 400 MHz, δ ppm): 10.51 (brs, 1H), 7.85 (m, 1H), 7.79 (d, 1H, J=9.0 Hz), 7.76 (d, 1H, J=2.0 Hz), 7.65 (d, 1H, J=1.6 Hz), 7.31 (m, 1H), 7.15 (dd, 1H, J=9.0 Hz, J=2.0 Hz), 7.10 (m, 2H), 6.09 (m, 1H), 3.9 (brs, 1H), 3.36 (c, 4H, J=7.3 Hz), 2.91 (m, 2H), 2.53 (m, 2H), 1.78 (m, 4H), 1.52 (m, 4H), 1.26-1.19 (m, 8H).

$^{13}$C-NMR (CD$_3$Cl, 100 MHz, δ ppm): 165.4, 158.9, 150.4, 147.5, 136.1, 133.5, 127.7, 126.6, 124.2, 123.6, 122.1, 122.0, 120.7, 119.1, 117.7, 115.0, 111.7, 111.4, 48.9, 38.9, 33.2, 31.1, 29.3, 29.1, 28.5, 26.3, 26.1, 23.9, 22.3, 22.0. ESI-MS[M]$^+$ 503.

Example 14

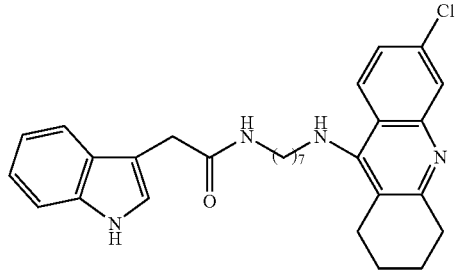

N-[7-(6-Chloro-1,2,3,4-tetrahydroacridin-9-ylamino)-heptyl]-2-(1H-indol-3-yl-acetamide Reagents: Indole-3-acetic acid (1.10 g, 6.3 mmol), THF anhydrous (50 ml), 1,1'-carbonyldiimidazol (1.07 g, 6.6 mmol), and 6-chloro-9-(8-aminoheptylamino)1,2,3,4-tetrahydroacridine (2.29 g, 6.6 mmol).

Purification: silica gel column chromatography (eluent: EtOAc/MeOH 50:1). Yellow solid. Yield: 2.48 g (80%).

$^1$H-NMR (CDCl$_3$, 400 MHz, δ ppm): 9.25 (brs, 1), 7.79 (d, 1H, J=9 Hz), 7.79 (d, 1H, J=2.0 Hz), 7.45 (d, 1H, J=8.0 Hz), 7.29 (d, 1H, J=8.0 Hz), 7.6 (dd, 1H, J=9 Hz, J=2.0 Hz), 7.11 (t, 1H, J=8.0 Hz), 7.03 (t, 1H, J=8.0 Hz), 7.03 (s, 1H), 5.71 (t, 1H, J=5.5 Hz), 3.82 (brs, 1H), 3.65 (s, 2H), 3.34 (t, 2H, J=7.0 Hz), 3.08 (c, 2H, J=6.6 Hz), 2.93 (brs, 2H), 2.56 (brs, 2H), 1.81 (m, 4H), 1.48 (m, 2 Hz), 1.28-1.06 (m, 8H).

$^{13}$C-NMR (CD$_3$Cl, 100 MHz, δ ppm): 171.4, 159.4, 150.6, 148.0, 136.4, 133.7, 127.2, 126.8, 124.4, 123.9, 123.7, 122.2, 119.6, 118.4, 118.2, 115.5, 111.3, 108.5, 49.3, 39.2, 33.7, 33.3, 31.4, 29.1, 28.6, 26.5, 26.3, 24.3, 22.7, 22.4. ESI-MS [M]$^+$ 503.

Example 15

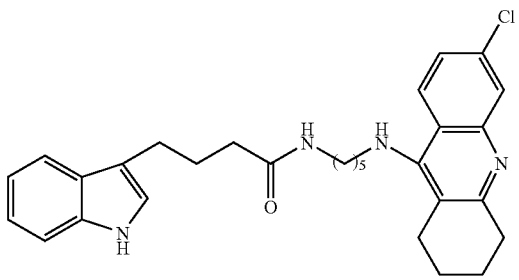

N-[5-(6-Chloro-1,2,3,4,-tetrahydro-acridin-9-ylamino)-pentyl]-4-(1H-indol-3-yl)-butyramide Reagents: Indole-3-butyric acid (134 mg, 0.66 mmol), THF anhydrous (10 ml), 1,1'-carbonyldiimidazol (107 mg, 0.66 mmol), and 6-chloro-9-(5-aminopentylamino)-1,2,3,4-tetrahydroacridine (200 mg, 0.63 mmol).

Purification: silica gel column chromatography using EtOAc/MeOH (100:1). Yellow solid. Yield: 220 mg (44%).

$^1$H-NMR (CDCl$_3$, 400 MHz, δ ppm): 8.47 (brs, 1H), 7.84 (d, 1H, J=1.9 Hz), 7.83 (d, 1H, J=10.0 Hz), 7.54 (d, 1H, J=7.4 Hz), 7.30 (d, 1H, J=7.4 Hz), 7.21 (dd, 1H, J=9.0 Hz, J=1.9 Hz), 7.13 (td, 1H, J=7.4 Hz, J=1.2 Hz), 7.05 (td, 1H, J=7.4 Hz, 0.1=1.2 Hz), 6.10 (d, 1H, J=2.4 Hz), 5.52 (t, 1H, 5.4 Hz), 3.91 (brs, 1H), 3.40 (m, 2H), 3.18 (c, 2H, J=6.4 Hz), 2.98 (brs, 2H), 2.76 (t, 2H, J=7.0 Hz), 2.60 (brs, 2H), 2.18 (t, 2H, J=7.0 Hz), 2.02 (m, 2H), 1.85 (m, 4 H), 1.61 (m, 2H), 1.45 (m, 2H), 1.36-1.31 (m, 2H).

$^{13}$C-NMR (CD$_3$Cl, 100 MHz, δ ppm): 173.3, 159.8, 150.8, 148.3, 136.5, 134.1, 127.6, 127;6, 124.7, 124.4, 122.0, 122.7, 119.2, 118.9, 118.6, 116.0, 115.6, 111.3, 49.5, 39.2, 36.4, 34.2, 31.4, 29.6, 26.3, 24.7, 24.7, 24.3, 23.0, 22.8. ESI-MS [M]$^+$ 503.

Example 16

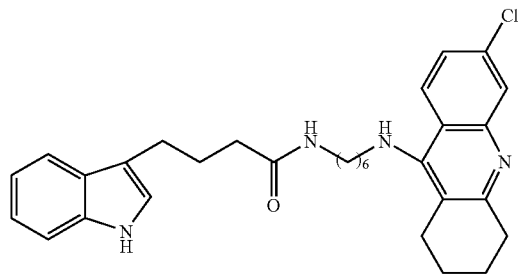

N-[6-(6-Chloro-1,2,3,4-tetrahydro-acridin-9-ylamino)-hexyl]4-(1H-Indol-3-yl)-butyramide Reagents: Indole-3-butyric acid (134 mg, 0.66 mmol), THF anhydrous (8 ml), 1,1'-carbonyldiimidazol (107 mg, 0.66 mmol), and 6-chloro-9-(5-aminohexylamino)-1,2,3,4-tetrahydroacridine (200 mg, 0.63 mmol).

Purification: silica gel column chromatography using DCM/MeOH (20:1, 20:1+0.01% NH$_3$). Yellow solid. Yield: 163 mg (48%).

$^1$H-NMR (CDCl$_3$, 400 MHz, δ ppm): 8.93 (brs, 1H), 7.85 (d, 1H, J=1.9 Hz), 7.84 (d, 1H, J=9.0 Hz), 7.51 (d, 1H, J=8.0 Hz), 7.29 (d, 1H, J=8.0 Hz), 7.20 (dd, 1H, J=9.0 Hz, J=2.0 Hz), 7.10 (t, 1H, J=7.5 Hz,), 7.02 (t, 1H, 7.5 Hz), 6.87 (d, 1H, J=1.4 Hz), 5.80 (brs, 1H), 4.12 (brs, 1H), 3.41 (t, 2H, J=7.4 Hz), 3.16 (c, 2H, J=6.6 Hz), 2.97 brs, 2H), 2.72 (t, 2H, J=7.4), 2.56 (brs, 2H), 2.17 (t, 2H, J=7.4 Hz), 1.99 (m, 2H), 1.83 (m, 4H), 1.56 (m, 2H), 1.41 (m, 2H), 1.35-1.21 (m, 4H).

$^{13}$C-NMR (CD$_3$Cl, 100 MHz, δ ppm): 173.6, 159.2, 151.4, 147.7, 136.7, 134.5, 127.6, 126.9, 125.1, 124.5, 122.0, 121.9, 120.0, 118.9, 118.3, 115.6, 115.4, 111.5, 49.5, 39.4, 36.5, 33.7, 31.8, 29.8, 26.7, 26.6, 26.4, 24.8, 24.7, 23.0, 22.7. ESI-MS[M]$^+$ 517.

Example 17

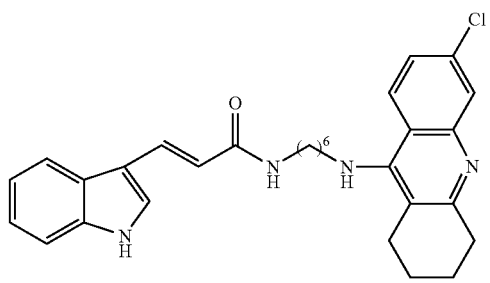

N-[6-(6-Chloro-1,2,3,4-tetrahydro-acridin-9-ylamino)-hexyl]-3-(1H-indol-3-yl)-acrylamide Reagents: Indole-3-acrylic acid (88 mg, 0.47 mmol), THF anhydrous (6 ml), 1,1'-carbonyldiimidazol (76 mg, 0.47 mmol), and 6-chloro-9-(5-aminohexylamino)-1,2,3,4-tetrahydroacridine (150 mg, 0.45 mmol).

Purification: silica gel column chromatography using EtOAc/MeOH (100:1, 100:1+0.1% NH₃). Yellow solid. Yield: 20 mg (8%).

¹H-NMR (CDCl₃, 400 MHz, δ ppm): 8.93 (brs, 1H), 7.83-7.76 (m, 4H), 7.33-732 (m, 2H), 7.19-7.08 (m, 3H), 6.35 (d, 1H, J=15.0H), 5.79 (t, 1H, J=5.9 Hz), 3.92 (brs, 1H), 3.38 (t, 2H, J=7.0 Hz), 3.33 (c, 2H, J=6.6 Hz), 2.94 (brs, 2H), 2.56 brs, 2H), 1.81 (m, 4H), 1.61-1.36 (m, 4H), 1.32 (m, 4H).

¹³C-NMR (CD₃Cl, 100 MHz, δ ppm): 167.8, 159.4, 151.0, 147.9, 137.5, 134.8, 134.2, 129.0, 127.0, 125.4, 124.9, 124.3, 122.8, 120.9, 120.2, 118.3, 115.6, 113.1, 112.2, 49.4, 39.6, 33.8, 31.7, 29.8, 26.7, 26.6, 24.6, 22.9, 22.6. ESI-MS[M]⁺ 50I.

Example 18

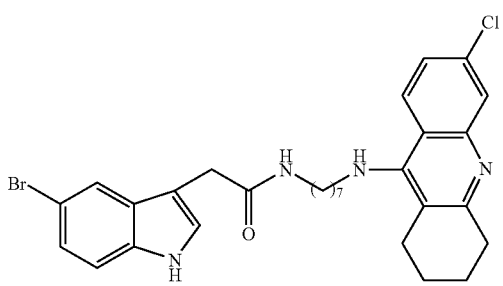

2-(5-Bromo-1H-indol-3-yl)-N-[7-(6-chloro-1,2,3,4-tetrahydro-acridin-9-ylamino)-heptyl]-acetamide Reagents: 5-Bromoindole-3-acetic acid (155 mg, 0.61 mmol), THF anhydrous (10 ml), 1,1'-carbonyldiimidazol (99 mg, 0.61 mmol), and 6-chloro-9-(8-aminoheptylamino)-1,2,3,4-tetrahydroacridine (200 mg, 0.58 mmol).

Purification: silica gel column chromatography (eluent: EtOAc/MeOH 50:1). Yellow solid. Yield: 185 mg (54%).

¹H-NMR (CDCl₃, 400 MHz, δ ppm): 9.36 (brs, 1H), 7.86 (d, 1H, J=9.0 Hz), 7.83 (d, 1H, J=2.3Hz), 7.63 (t, 1H, J=0.8 Hz), 7.23 (m, 1H), 7.21 (m, 2H), 7.09 (d, 1H, J=2.3 Hz), 5.72 (t, 1H, J=5.8 Hz), 3.95 (brs, 1H), 3.64 (s, 2H), 3.42 (t, 21, J=7.2 Hz), 3.15 (c, 2H, J=6.6 Hz), 2.98 (brs, 2H), 2.61 (brs, 2H), 1.86 (m, 4H), 1.56 (m, 2H), 1.34 (m, 2H), 1.30-1.17 (m, 4H), 1.14 (m, 2H).

¹³C-NMR (CD₃Cl, 100 MHz, δ ppm): 171.2, 159.5, 151.09, 148.1, 135.2, 134.2, 128.9, 127.3, 125.4, 125.3, 124.9, 124.3, 121.4, 118.4, 115.7, 113.2, 113.1, 108.6, 49.6, 39.6, 34.0, 33.5, 31.8, 29.5, 29.0, 26.8, 26.7, 24.6, 23.0, 22.7. ESI-MS[M+1, ⁷⁹Br]⁺581, [M+1, ⁸¹Br]⁺ 583.

Example 19

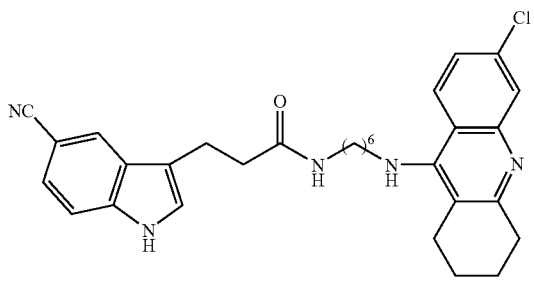

N-[6-(6-Chloro-1,2,3,4-tetrahydro-acridin-9-ylamino)-hexyl]-3-(5-isocyano-1H-indol-3-yl)-propionamide Reagents: 5-Cyanoindole-3-propionic acid (111 mg, 0.52 mmol), THF anhydrous (10 ml), 1,1'-carbonyldiimidazol (84 mg, 0.52 mmol), and 6-chloro-9-(8-aminoheptylamino) 1,2,3,4-tetrahydroacridine (164 mg, 0.49 mmol).

Purification: silica gel column chromatography (eluent: EtOAc/MeOH 50:1). Yellow solid. Yield: 60 mg (22%).

¹H-NMR (CDCl₃, 400 MHz, δ ppm): 9.48 (brs, 1H), 7.89 (s, 1H), 7.87 (d, 1H, J=9.0 Hz), 7.82 (d, 1H, J=2.1 Hz), 7.33 (brs, 2H), 7.23 (dd, 1H, J=9.0 Hz, J=2, 1 Hz), 7.10 (brs, 1H), 5.70 (t, 1H, J=5.6 Hz), 4.00 (brs, 1H), 3.44 (t, 2H, J=7.2 Hz), 3.18 (c, 2H, J=6.6 Hz), 3.08 (t, 2H, J=7.2 Hz), 2.98 (brs, 2H), 2.62 (brs, 2H), 2.52 (t, 2H, J=7.4 Hz), 1.88 (m, 4H), 1.58 (m, 2H), 1.42-1.24 (m, 4H), 1.40-1.24 (m, 4H), 1.23-1.18 (m, 2H).

¹³C-NMR (CD₃Cl, 100 MHz, δ ppm): 172.5, 159.7, 151.2, 148.3, 138.3, 135.3, 134.42, 127.6, 127.4, 125.0, 124.9, 124.7, 124.6, 124.4, 121.1, 118.7, 116.2, 116.1, 112.4, 102.5, 49.6, 39.6, 37.6, 34.2, 31.9, 29.8, 26.7, 24.9, 23.2, 22.9, 21.3. ESI-MS[M]⁺ 528.

Example 20

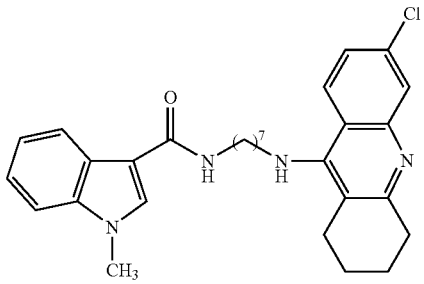

1H-Methylindole-3-carboxylic acid [7-(6-chloro-1,2,3,4-tetrahydroacridin-9-ylamino)-heptyl]-amide Reagents: 1-Methylindole-3-carboxylic acid (212 mg, 1.21 mmol), THF anhydrous (10 ml), 1,1'-carbonyldiimidazol (197 mg, 1.21 mmol), and 6-chloro-9-(8-aminoheptylamino)-1,2,3,4-tetrahydroacridine (400 mg, 1.16 mmol).

Purification: silica gel column chromatography (eluent: EtOAc/MeOH 50:1). Yellow solid. Yield: 45 mg (8%).

¹H-NMR (CDCl₃, 400 MHz, δ ppm): 7.88 (d, 1H, J=7.0 Hz), 7.86 (d, 1H, J=9 Hz), 7.84 (d, 1H, J=2.3 Hz), 7.63 (s, 1H), 7.33 (d, 1H, J=7.0 Hz), 7.28-7.20 (m, 3H, 5.97 (t, 1H, J=5.5 Hz), 3.9 (brs, 1H), 3.44 (m, 4H), 2.99 (m, 2H), 2.62 (m, 2H), 1.87 (m, 4H), 1.59 (m, 4H), 1.36 (m, 6H).

¹³C-NMR (CD₃Cl, 100 MHz, δ ppm): 165.3, 159.7, 150.9, 148.3, 137.3, 134.0, 132.4, 127.7, 125.3, 124.7, 124.3, 122.6, 121.5, 120.0, 118.5, 115.9, 111.1, 110.2, 49.7, 39.5, 34.2, 33.4, 31.8, 30.0, 29.1, 27.0, 26.9, 24.7, 23.0, 22.8. ESI-MS [M]⁺ 503.

Example 21

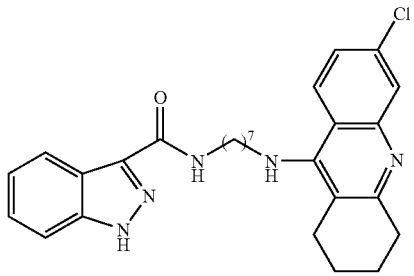

1H-Indazole-3-carboxylic acid [7-(6-chloro-1,2,3,4-tetrahydroacridin-9-ylamino) heptyl]-amide Reagents: Indazole-3-carboxylic acid (162 mg, 1.00 mmol), THF anhydrous (5 ml), 1,1'-carbonyldiimidazol (170 mg, 1.05 mmol), and 6-chloro-9-(8-aminoheptylamino)1,2,3,4-tetrahydroacridine (364 mg, 1.05 mmol).

Purification: silica gel column chromatography (eluent: EtOAc/MeOH 50:1); Yellow solid. Yield: 6 mg (1%).

$^1$H-NMR (CDCl$_3$, 400 MHz δ ppm): 11.26 (brs, 1H), 8.34 (d, 1H, J=8.0 Hz), 7.84 (d, 1H, J=2.0 Hz), 7.82 (d, 1H, J=9.0 Hz), 7.43 (dd, 1H, J=8.0 Hz), 7.5 (t, 1H, j=7 Hz), 7.23-7.17 (m, 2H), 7.03 (t, 1H, J=5.5 Hz), 3.9 (brs, 1H), 3.42 (m, 4H), 2.96 (brs, 2H), 2.58 (brs, 2H), 1.82 (m, 4H), 1.57 (m, 4H), 1.32 (m, 6H).

$^{13}$C-NMR (CD$_3$Cl, 100 MHz, δ ppm): 162.9, 159.6, 151.1, 148.2, 141.5, 139.6, 134.2, 127.5, 127.4, 124.8, 124.4, 122.9, 122.8, 122.1, 118.5, 115.8, 109.9, 49.7, 39.0, 34.1, 31.8, 29.8, 29.1, 26.9, 26.8, 24.7, 23.0, 22.7. ESI-MS[M]$^+$ 490.

Example 22

The indole-tacrine carbamate derivatives were synthesized following a similar method to that reported in the literature: Bruce, A.; Spangle, L. A.; Kaldor, S. W.; *Tetrahedron Letters*, 1996, 7, 937-940. The synthetic strategy is summarized in scheme 2.

Synthesis of Intermediate Carbonic Acid 2-(1H-indol-3-yl)-ethyl Ester 4-nitro-phenyl Ester To a solution of 2-(1H-indol-3-yl)-ethanol (1600 mg, 9.92 mmol), in N-methyl morpholine (2000 m g, 19.84 mmol), was added p-nitrophenyl chloroformate (4000 mg, 19.84 mmol), and the mixture was stirred for 24 hours at room temperature. Water was added and the mixture extracted with dichloromethane. Evaporation of the solvent gave a residue which was purified by silica gel column chromatography using a mixture of DCM/Hx (3:1) as eluent to produce 1034 mg (32%) of the title compound as a yellow solid.

General Synthesis of Carbamate Derivatives:

To a solution of the carbonic acid 2-(1H-indol-3-yl)-ethyl ester 4-nitro-phenyl ester, was added a solution of the corresponding alkylaminotetrahydroacridine in DMF, in presence of DMAP, and the resulting mixture was stirred for 24 hours at room temperature. After evaporation of the solvent under reduced pressure water was added and the mixture extracted with dichloromethane. Evaporation of the solvent gave a residue which was purified by silica gel column chromatography as indicated bellow for each case.

Example 23

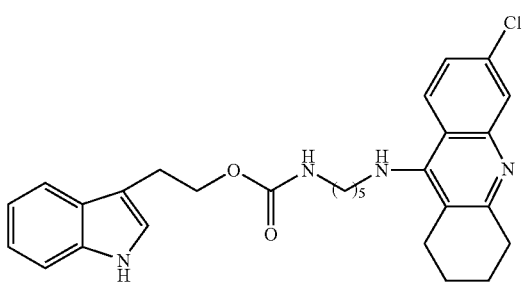

[5-(6-Chloro-1,2,3,4-tetrahydro-acridin-9-ylamino)-pentyl]1-carbamic Acid 2-(1H-indol-3-yl)ethyl Ester Reagents: N1-(6-Chloro-1,2,3,4-tetrahydro-acridin-9-yl)-pentane-1,5-diamine (500 mg, 1.58 mmol), carbonic acid 2-(1H-indol-3-yl)-ethyl ester 4-nitro-phenyl ester (260 mg 0.79 mmol), DMAP (1930 mg, 1.58 mmol).

Purification: silica gel chromatography using DCM/MeOH (7:0.5) as eluent. Yield: 126 mg (32%).

$^1$H-NMR (CDCl$_3$, 400 MHz, δ ppm): 8.51 (brs, 1H), 7.86 (m, 2H), 7.57 (m, 1H, J=8.0 Hz), 7.28 (m, 1H, J=8.0 Hz), 7.21-7.23 (m, 1H), 7.14-7.10 (m, 1H), 7.07-7.03 (m, 1H), 6.97-6.82 (m, 1H), 4.77 (brs, 1H), 4.33-4.30 (m, 2H), 4.04 (m, 2H), 3.14-3.13 (m, 2H), 3.05-2.98 (m, 4H), 2.58 (brs, 2H), 1.87-1.83 (m, 4H), 1.62-1.61 (m, 2H), 1.49-1.47 (m, 2H), 1.37-1.36 (m, 2H).

$^{13}$C-NMR (CD$_3$Cl, 100 MHz, δ ppm): 165.7, 159.4, 151.3, 1.47.7, 136.5, 134.6, 127.7, 127.0, 124.9, 124.6, 122.3, 122.1, 119.4, 118.9, 118.3, 116.3, 115.8, 112.2, 49.5, 40.8, 33.7, 31.5, 30.0, 25.4, 24.7, 24.2, 23.0, 22.7.

ESI-MS[M+H]$^+$505.1

Example 24

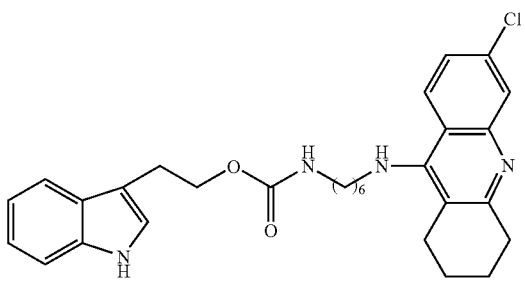

[6-(6-Chloro-1,2,3,4-tetrahydro-acridin-9-ylamino)-hexyl]-carbamic Acid 2-(1h-indol-3-yl)ethyl Ester Reagents: N1-(6-Chloro-1,2,3,4-tetrahydro-acridin-9-yl)-hexane-1,6-d amine (610 mg, 1.84 mmol), carbonic acid 2-(1H-indol-3-yl)-ethyl ester 4-nitro-phenyl ester (300 mg, 0.92 mmol), DMAP (225 mg, 1.84 mmol).

Purification: DCM/MeOH (7:0.5). Yield: 100 mg (21%).

$^1$H-NMR (CDCl$_3$, 400 MHz, δ ppm): 8.25 (brs, 1H), 7.90-7.87 (m, 2H), 7.62 (d, 1H, J=8.0 Hz), 7.34 (d, 1H, J=8.0 Hz), 7.30-7.25 (m, 2H), 7.20-7.16 (m, 1H), 7.13-7.08 (m, 1H), 7.03-7.02 (m, 1H), 4.67 (brs, 1H), 4.36-4.33 (m, 2H, 3.46 (bs, 2H), 3.17-3.03 (m, 6H), 2.66 (brs, 2H), 1.92-1.90 (m, 4H), 1.66-1.33 (m, 6H).

$^{13}$C-NMR (CD$_3$Cl, 100 MHz, δ ppm): 159.5, 156.7, 150.7, 148.0, 136.1, 134.0, 127.5, 124.5, 124.2, 122.0, 119.3, 118.7, 118.3, 115.7, 112.1, 111.1, 65.0, 49.4, 40.6, 34.0, 31.6, 30.0, 26.4, 26.3, 25.2, 24.5, 23.0, 22.6.

ESI-MS[M+H]$^+$519.1.

Example 25

[7-(3-Chloro-1,2,3,4-tetrahydro-acridin-9-ylamino)-heptyl]-carbamic Acid 2-(1H-indol-3-yl)ethyl Ester Reagents: N1-(6-Chloro-1,2,3,4-tetrahydro-acridin-9-yl)-heptane-1,7-diamine (344 mg, 1.0 mmol), carbonic acid 2-(1H-indol-3-yl)-ethyl ester 4-nitro-phenyl ester (166 mg, 0.5 mmol), DMAP (122 mg, 1.0 mmol).

Purification: chromatography purification using DCM/MeOH (7:0.5) as eluent. Yield: 70 mg (40%) crystalline solid, colour amber.

$^1$H-NMR (CDCl$_3$, 400 MHz, δ ppm): 8.25 (brs, 1H), 7.90-7.88 (m, 2H), 7.62 (d, 1H, J=8.0 Hz), 7.34 (d, 1H, J=8.0 Hz), 7.30-7.25 (m, 2H), 7.20-7.15 (m, 1H), 7.13-7.08, (m, 1H), 7.03-7.02 (m, 1H), 4.71 (brs, 1H), 4.35-4.32 (m, 2H), 3.5-3.45 (n, 2H), 3.11-3.12 (m, 2H), 3.09-3.06 (m, 2H), 3.03 (brs, 2H), 2.64 (brs, 2H), 1.91-1.88 (m, 4H), 1.64-1.60 (m, 2H), 1.47-1.44 (m, 2H), 1.31-1.25 (m, 6H).

$^{13}$C-NMR (CD$_3$Cl, 100 MHz, δ ppm): 159.6, 156.9, 151.2, 148.2, 136.4, 134.3, 127.7, 127.5, 124.9, 124.5, 122.3, 122.2, 119.0, 118.5, 115.8, 112.3, 111.4, 65.1, 49.8, 41.1, 34.0, 31.9, 30.2, 29.2, 27.0, 26.7, 25.4, 24.7, 23.1, 22.8.

ESI-MS[M+H]$^+$533.10.

Example 26

Comparative Example

The N-[2-3(Indolyl)ethyl]-6-chlorotacrine having a short linker was synthesized following the reported method (Ming-Kuan, H. U. and Jiajiu, S. WO 01/17529) and its characterization by 1H NMR and $^{13}$C NMR was in agreement with that in the literature (same reference).

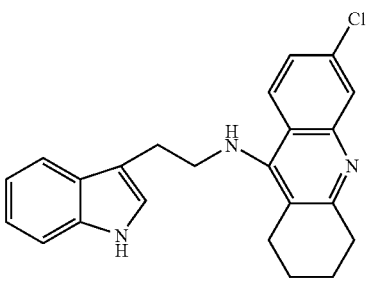

Example 27

Biological Evaluation

Acetylcholinesterase (AChE) Inhibition (from Bovine Erythrocytes)

AChE inhibitory activity was evaluated at 30° C. by the colorimetric method reported by Ellman [Ellman, G. L.; Courtney, K. D.; Andres, B.; Featherstone, R. M. *Biochem. Pharmacol.* 1961, 7, 88-95]. The assay solution consisted of 0.1 M phosphate buffer pH 8, 0.3 mM 5,5'-dithiobis(2-nitrobenzoic acid) (DTNB, Ellman's reagent), 0.02 unit AChE (Sigma Chemical Co. from bovine erythrocytes), and 0.5 mM acetylthiocholine iodide as the substrate of the enzymatic reaction. The compounds tested were added to the assay solution and pre incubated with the enzyme for 5 min at 30° C. After that period, the substrate was added. The absorbance changes at 405 nm were recorded for 5 min with a microplate reader Digiscan 340T, the reaction rates were compared, and the percent inhibition due to the presence of test compounds was calculated. The reaction rate was calculated with, at least, triplicate measurements, and the percent inhibition due to the presence of test compound was calculated relative to the compound-free control. The compound concentration producing 50% of AChE inhibition (IC$_{50}$) was determined. The results shown in table 1.

Butyrylcholinesterase (BuChE) Inhibition (from Human Serum)

BuChE inhibitory activity was evaluated at 30° C. by the colorimetric method reported by Ellman. The assay solution consisted of 0.01 unit BuChE from human serum, 0.1 M sodium phosphate buffer pH 8, 0.3 mM 5,5'-dithiobis(2-nitrobenzoic acid) (DTNB, Ellman's reagent), and 0.5 mM butyrylthiocholine iodide as the substrate of the enzymatic reaction. Enzyme activity was determined by measuring the absorbance at 405 nm during 5 minutes with a microplate reader Digiscan 340T. The tested compounds were preincubated with the enzyme for 10 minutes at 30° C. The reaction rate was calculated with, at least, triplicate measurements. The IC$_{50}$ is defined as the concentration of each compound that reduces a 50% the enzymatic activity with respect to that without inhibitor. The results are shown in table 1.

Toxicity Measurement

The cytotoxicity effect of the molecules was tested in the human neuroblastoma cell line SH-SY5Y. These cells were cultured in 96-well plates in DULBECCO'S MOD EAGLE medium, supplemented with 10% fetal bovine serum and 1% penicillin/streptomycin, and grown in a 5% $CO_2$ humidified incubator at 37° C.

The cells were plated at $10^4$ cells for each well, at least, 48 hours before the toxicity measure. Cells were exposed for 24 hours to the compounds at different concentrations (from $10^{-5}$ to $10^{-9}$), quantitative assessment of cell death was made by measurement of the intracellular enzyme lactate dehydrogenase (LDH) (citotoxicity detection kit, Roche). The quantity of LDH was evaluated in a microplate reader Anthos 2010, at 492 and 620 nm. Controls were taken as 100% viability. The results are shown in table 1.

Propidium Competition

Propidium exhibits an increase in fluorescence on binding to AChE peripheral site, making it a useful probe for competitive ligand binding to the enzyme.

Fluorescence was measured in a Fluostar optima plate reader (BMG). Measurements were carried out in 100 μl solution volume, in 96-well plates. The buffer used wad 1 mM Tris/HCl, pH 8.0. 10 μM AchE was incubated, at least 6 hours, with the molecules at different concentrations. 20 μM propidium iodide was added 10 min before fluorescence measurement. The excitation wavelength was 485 nm, and that of emission, 620 nm. The results are shown in table 1.

TABLE 1

| Compound | Structure | $IC_{50}$ AChE (nM) | $IC_{50}$ BuChE (nM) | Toxicity (μM) | Propidium competition (μM) |
|---|---|---|---|---|---|
| 1 | 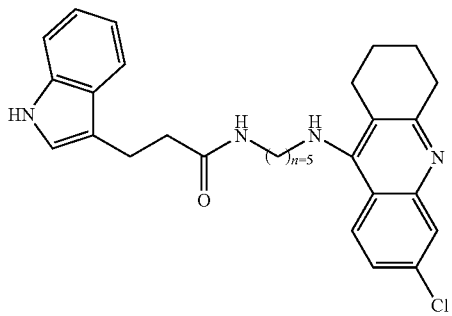 | 4 | 100 | >100 | >100 |
| 2 | 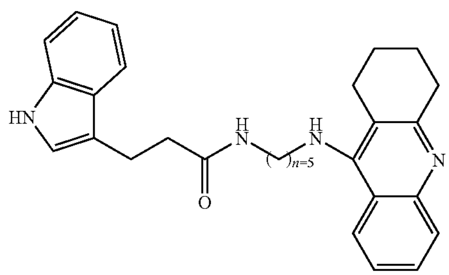 | 70 | 1 | >100 | 10 |
| 3 | 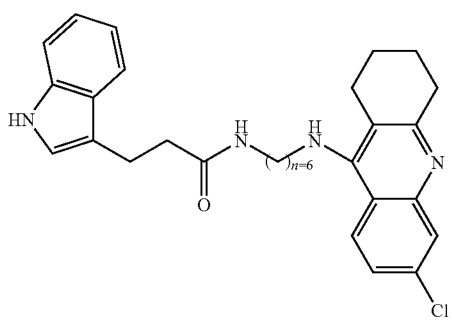 | 0.02 | 2.9 | 100 | 1000 |
| 4 | 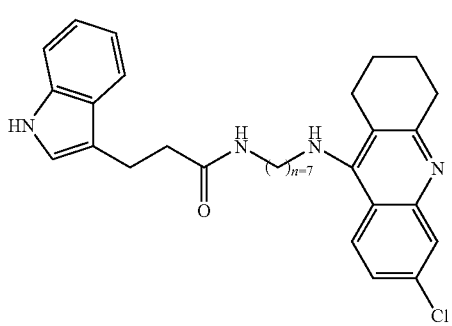 | 0.06 | 0.1 | 10 | 10 |

TABLE 1-continued
| Compound | Structure | IC$_{50}$ AChE (nM) | IC$_{50}$ BuChE (nM) | Toxicity (μM) | Propidium competition (μM) |
|---|---|---|---|---|---|
| 5 | 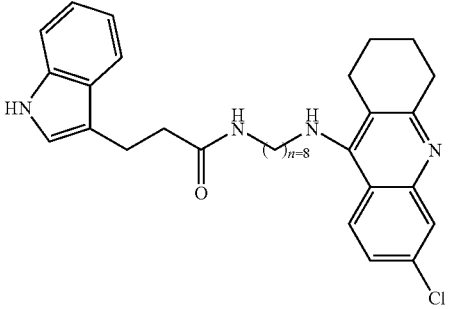 | 0.5 | 5.7 | 10 | 10 |
| 6 | 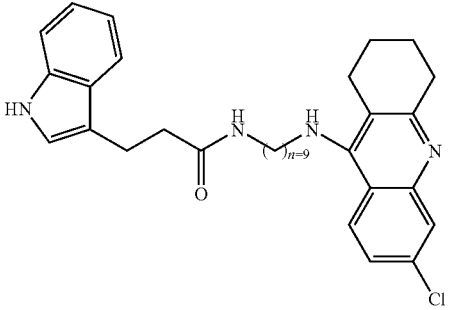 | 4.4 | 9.6 | >100 | >100 |
| 7 | 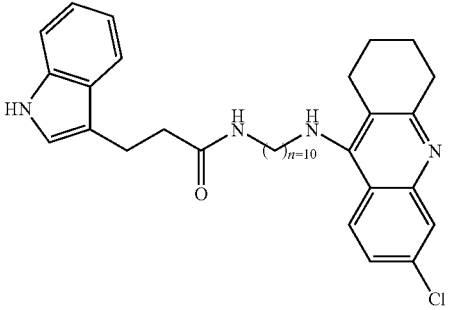 | 21.9 | 54 | >100 | 10 |
| 8 | 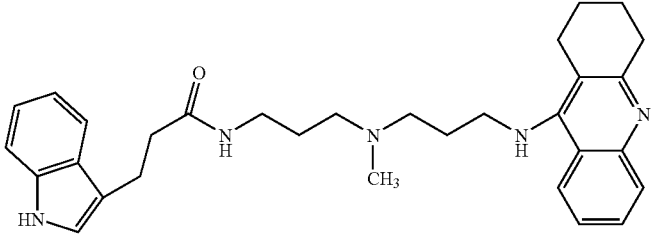 | 147 | 0.03 | >100 | 1000 |
| 9 | 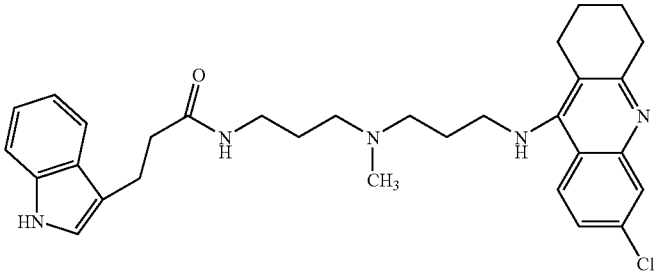 | 2.88 | 7.57 | >100 | 10 |

TABLE 1-continued

| Compound | Structure | IC$_{50}$ AChE (nM) | IC$_{50}$ BuChE (nM) | Toxicity (µM) | Propidium competition (µM) |
|---|---|---|---|---|---|
| 10 | 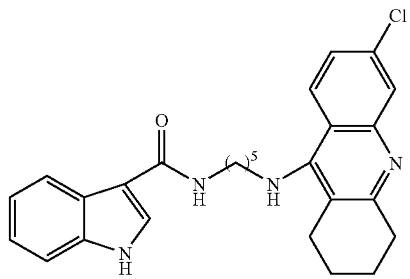 | 180 | 9.5 | >10 | 100 |
| 11 | 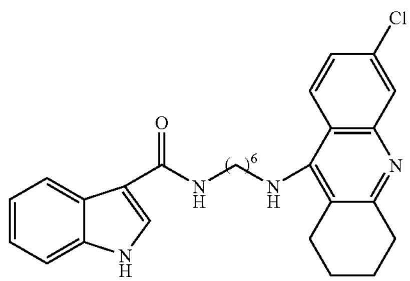 | 33 | 1.7 | >10 | 100 |
| 12 | 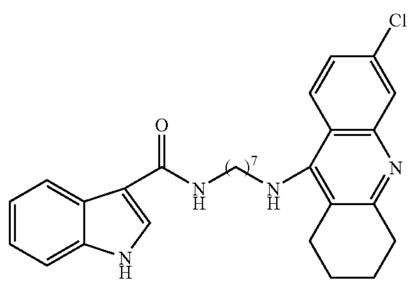 | 36 | 19 | >10 | 100 |
| 13 | 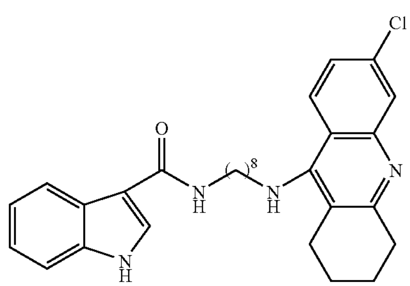 | 46 | 22.4 | >10 | 10 |
| 14 | 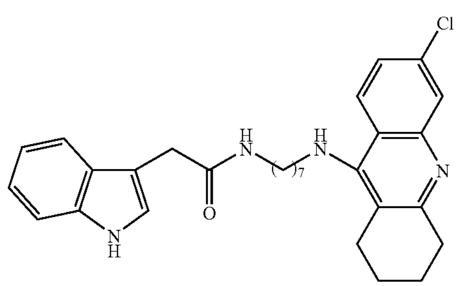 | 0.18 | 11.7 | >10 | 10 |

TABLE 1-continued

| Compound | Structure | IC$_{50}$ AChE (nM) | IC$_{50}$ BuChE (nM) | Toxicity (μM) | Propidium competition (μM) |
|---|---|---|---|---|---|
| 15 | 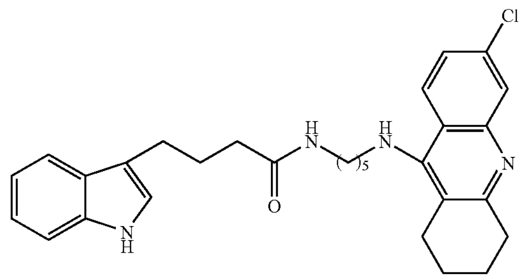 | 0.34 | 3.2 | >10 | 10 |
| 16 | 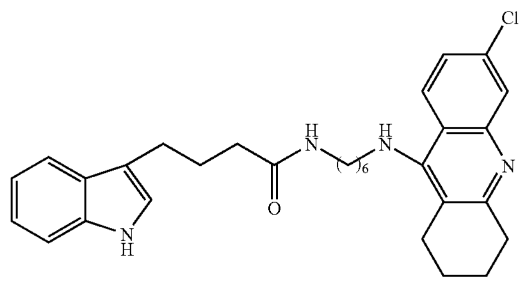 | 0.48 | 5.6 | >10 | 100 |
| 17 | 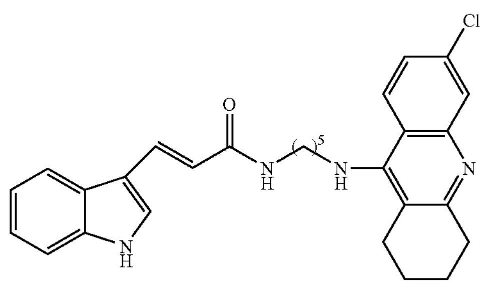 | 18 | 77 | >10 | 10 |
| 18 | 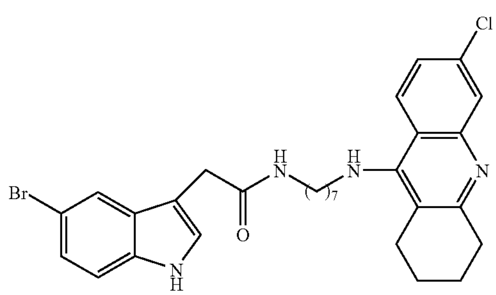 | 0.63 | 1.7 | >10 | 100 |
| 19 | 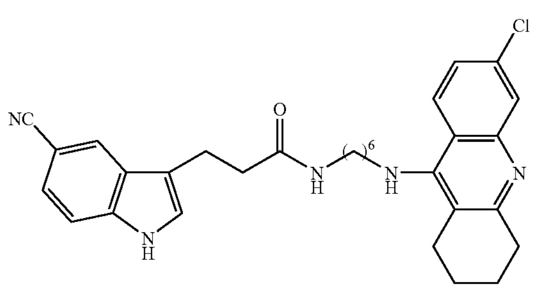 | 0.72 | 11.7 | >10 | 100 |

TABLE 1-continued
| Compound | Structure | IC$_{50}$ AChE (nM) | IC$_{50}$ BuChE (nM) | Toxicity (μM) | Propidium competition (μM) |
|---|---|---|---|---|---|
| 20 | 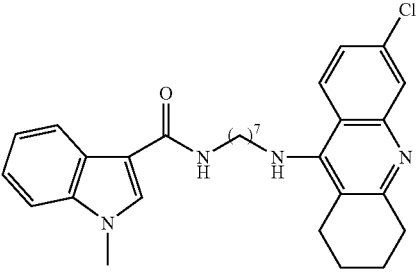 | 10.9 | 206 | >10 | 100 |
| 21 | 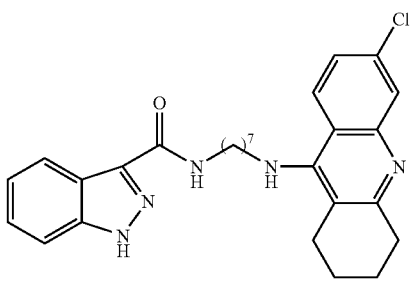 | 95 | 79 | >10 | 100 |
| 23 | 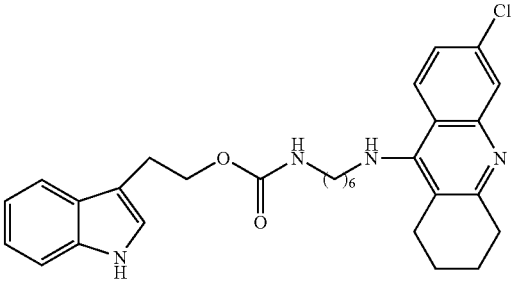 | 1.5 | 13.6 | >10 | 100 |
| 24 | 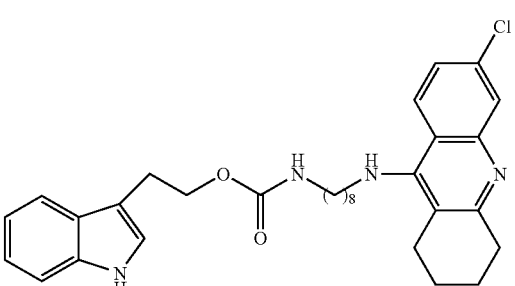 | 0.7 | 3.2 | >10 | 100 |
| 25 | 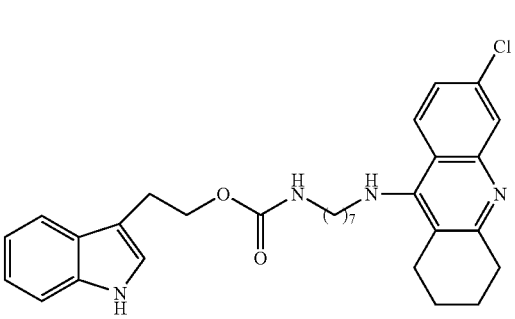 | 3 | 59 | >10 | 10 |

TABLE 1-continued

| Compound | Structure | IC$_{50}$ AChE (nM) | IC$_{50}$ BuChE (nM) | Toxicity (μM) | Propidium competition (μM) |
|---|---|---|---|---|---|
| Comparative Example | 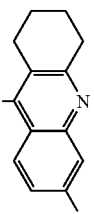 | 537 | | | |

Example 27

Inhibition of β-Amyloid Aggregation

The generation of AChE-Aβ complexes were carried out as described previously [Alvarez, A et al. *J. Neurosci.*, 1998, 18, 3213-3223; Muñoz, F. J.; Inestrosa, N. C. *FEBS Let.*, 1999, 450, 205-209]. Stock solutions of Aβ$_{1-40}$ (rPeptide, Georgia USA) at 3.5 mM were dissolved in PBS (pH 7.4) after HFIP treatment to obtain monomeric starting material, according to manufacture's recommendations. For co-incubation experiments, 0.1 mM of peptide was mixed with human recombinant acetylcholinesterase (huAchE, Sigma-Aldrich), in the same buffer at molar ratio Aβ:huAChE 200:1, and stirred for 48 hours in a microtiter plate at room temperature. The fibrils obtained were characterized by Congo Red (CR) binding.

For the inhibition of β-amyloid aggregation, the compounds tested were used at the IC$_{50}$ defined in the previous paragraph of the biological evaluation, 50 μM propidium iodide was used as reference [Inestrosa, N. C et al., *J. Neuron*, 1996, 16, 881-891].

To quantify the amount of fibrils aggregated, the binding to CR was done as described [Klunk, W E.; Pettegrew, J W.; Abraham, D J. *J. Hystochem Cytochem.*, 1989, 8, 1293-1297]. Briefly, 5.5 μl aliquot of the aggregation mixture was added to 132 μl of a 25 μM CR solution (100 mM phosphate buffer pH 7.4, 150 mM NaCl), and incubated for 30 minutes at room temperature. Absorbance was measured at 480 and 540 nm and the molarity of aggregates calculated by CR(M)=(A$_{540}$/25295)−(A$_{480}$/46306).

In the conditions above described, the indol compound derivative's 3 and 8 showed a 15% and 17% reduction respectively, in the β-amyloid-huAChE aggregation complex. The peripheral inhibitor propidium iodide used as reference did show a 10% reduction.

We claim:

1. A compound having the following formula

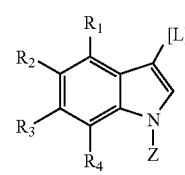

or a tautomer, or a pharmaceutically acceptable salt thereof;

wherein
each of R$_1$, R$_2$, R$_3$, R$_4$, and R$_5$ is, independently, selected from the group consisting of hydrogen, —CN, and halogen;
Z is selected from the group consisting of hydrogen and unsubstituted alkyl;
-(L)$_k$-(L)$_m$-(L)$_n$-(L)$_q$-(L)$_x$-(L)$_w$- is selected from the formulae —(CH$_2$)$_k$—CO—NR$_a$—(CH$_2$)$_w$—,
—(CH$_2$)$_k$—NR$_a$—CO—(CH$_2$)$_w$—, —(CH$_2$)$_k$—CO—NR$_a$—(CH$_2$)$_q$—NR$_a$—(CH$_2$)$_w$,
—(CH$_2$)$_k$—NR$_a$—CO—(CH$_2$)$_q$—NR$_a$—(CH$_2$)$_w$—, and
—(CH$_2$)$_k$—O—CO—NR$_a$—(CH$_2$)$_w$—;
wherein:
R$_a$ is H or unsubstituted alkyl;
each of k, q and w is an integer independently selected from the group consisting of 0, 1, 2, 3, 4, 5, 6, 7, 8, 9 and 10, with the proviso that k+q+w is at least 4.

2. The compound of claim 1, wherein R$_1$, R$_2$, R$_3$, R$_4$, Z are each hydrogen; and R$_5$ is halogen.

3. The compound of claim 1, wherein -(L)$_k$-(L)$_m$-(L)$_n$-(L)$_q$-(L)$_x$-(L)$_w$- is of formula —(CH$_2$)$_k$—CONH—(CH$_2$)$_w$—, where the sum of k and w is in the range 6 to 10.

4. The compound of claim 3, wherein the sum of k and w is 7 to 9.

5. The compound of claim 4, wherein k is 1, 2 or 3.

6. A compound selected from the group consisting of:
N-[5-(6-Chloro-1,2,3,4-tetrahydro-acridin-9-ylamino)-pentyl]-3-(1H-indol-3-yl)-propionamide;
3-(1H-Indol-3-yl)-N-[5-(1,2,3,4-tetrahydro-acridin-9-ylamino)-pentyl]-propionamide;
N-[5-(6-Chloro-1,2,3,4-tetrahydro-acridin-9-ylamino)-hexyl]-3-(1H-indol-3-yl)-propionamide;
N-[7-(6-Chloro-1,2,3,4-tetrahydro-acridin-9-ylamino)-heptyl]-3-(1H-indol-3-yl)-propionamide;
N-[8-(6-Chloro-1,2,3,4-tetrahydro-acridin-9-ylamino)-octyl]-3-(1H-indol-3-yl)-propionamide;
N-[9-(6-Chloro-1,2,3,4-tetrahydro-acridin-9-ylamino)-nonyl]-3-(1H-indol-3-yl)-propionamide;
N-[10-(6-Chloro-1,2,3,4-tetrahydro-acridin-9-ylamino)-decyl]3-(1H-indol-3-yl)-propionamide;
N-(3-{[3-(1,2,3,4-tetrahydro-acridin-9-ylamino)-propyl]-methyl-amino}-propyl)-3-(1H-indol-3-yl)-propionamide;
N-(3-{[3-(6-chloro-1,2,3,4-tetrahydro-acridin-9-ylamino)-propyl]-methyl-amino}-propyl)-3-(1H-indol-3-yl)-propionamide;
1H-Indole-3-carboxylic acid [5-(6-chloro-1,2,3,4-tetrahydro-acridin-9-ylamino)-pentyl]-amide;

1H-Indole-3-carboxylic acid [6-(6-chloro-1,2,3,4-tetrahydro-acridin-9-ylamino)-hexyl]-amide;
1H-Indole-3-carboxylic acid [7-(6-chloro-1,2,3,4-tetrahydro-acridin-9-ylamino)-heptyl]-amide:
1H-Indole-3-carboxylic acid [8-(6-chloro-1,2,3,4-tetrahydro-acridin-9-ylamino)-octyl]-amide;
N-[7-(6-Chloro-1,2,3,4-tetrahydroacridin-9-ylamino)-heptyl]-2-(1H-indol-3-yl)-acetamide;
N-[5-(6-Chloro-1,2,3,4-tetrahydro-acridin-9-ylamino)-pentyl]-4-(1H-indol-3-yl)-butyramide;
N-[6-(6-Chloro-1,2,3,4-tetrahydro-acridin-9-ylamino)-hexyl]-4-(1H-indol-3-yl)-butyramide;
N-[6-(6-Chloro-1,2,3,4-tetrahydro-acridin-9-ylamino)-hexyl]-3-(1H-indol-3-yl)-acrylamide;
2-(5-Bromo- 1H-indol-3-yl)-N-[7-(6-chloro-1,2,3,4-tetrahydro-acridin-9-ylamino)-heptyl]-acetamide:
N-[6-(6-Chloro-1,2,3,4-tetrahydro-acridin-9-ylamino)-hexyl]-3-(5-isocyano-1H-indol-3-yl)-propionamide;
1H-Methylindole-3-carboxylic acid [7-(6-chloro-1,2,3,4-tetrahydroacridin-9-ylamino)-heptyl]-amide:
1H-Indazole-3-carboxylic acid [7-(6-chloro-1,2,3,4-tetrahydroacridin-9-ylamino)-heptyl]-amide;
[5-(6-Chloro-1,2,3,4-tetrahydro-acridin-9-ylamino)-pentyl]-carbamic acid 2-(1H-indol-3-yl)-ethyl ester;
[6-(6-Chloro-1,2,3,4-tetrahydro-acridin-9-ylamino)-hexyl]-carbamic acid 2-(1H-indol-3-yl)-ethyl ester and
[7-(3-Chloro-1,2,3,4-tetrahydro-acridin-9-ylamino)-heptyl]-carbamic acid 2-(1H-indol-3-yl)-ethyl ester.

7. A pharmaceutical composition which comprises a compound as claimed in claim 1 or a tautomer, or a pharmaceutically acceptable salt thereof, together with a pharmaceutically acceptable carrier, adjuvant or vehicle.

8. The pharmaceutical composition of claim 7 for oral administration.

9. The compound of claim 1, wherein $-(L)_k-(L)_m-(L)_n-(L)_q-(L)_x-(L)_w-$ is of the formulae $-(CH_2)_k-CO-NR_a-(CH_2)_q-NR_a-(CH_2)_w-$.

10. The compound of claim 1 wherein Z is selected from H and $CH_3$.

11. The compound of claim 10, wherein Z is H.

12. The compound of claim 1 wherein $R_1$, $R_3$ and $R_4$ are H.

13. The compound of claim 1 wherein $R_2$ is selected from H, -Hal, and —CN.

14. The compound of claim 1 wherein $R_5$ is halogen and $R_6$ is hydrogen.

15. The compound of claim 1 wherein $-(L)_k-(L)_m-(L)_n-(L)_q-(L)_x-(L)_w-$ has the formulae $-(CH_2)_k-CO-NR_a-(CH_2)_w-$ or $-(CH_2)_k-O-CO-NR_a-(CH_2)_w-$.

16. The compound of claim 15 wherein $R_a$ is H.

17. The compound of claim 15 wherein k is 1 or 2.

18. The compound of claim 17, wherein k is 2.

19. The compound of claim 1, wherein w is 6, 7, 8 or 9.

20. The compound of claim 19, wherein w is 6 or 7.

21. The compound of claim 1, wherein the sum of k, q and w is selected from 10 and 11.

* * * * *